United States Patent
Zhang et al.

(10) Patent No.: US 6,726,673 B1
(45) Date of Patent: *Apr. 27, 2004

(54) METHODS AND APPARATUS FOR IMPROVED ADMINISTRATION OF TESTOSTERONE PHARMACEUTICALS

(75) Inventors: Jie Zhang, Salt Lake City, UT (US); Hao Zhang, Midvale, UT (US); Wade A. Hull, Taylorsville, UT (US); Larry Rigby, Salt Lake City, UT (US)

(73) Assignee: Zars, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,313

(22) Filed: May 24, 1999

(51) Int. Cl.⁷ .................. A61M 31/00; A61N 1/30; A61F 7/00; A61F 13/00; A61L 15/16; A61K 9/70

(52) U.S. Cl. .................. 604/500; 604/20; 604/291; 424/447; 424/449

(58) Field of Search ............... 604/20, 46, 47, 604/48, 500, 501, 289, 290, 291, 304, 307, 113; 606/27–31; 424/443, 444, 447, 448, 449

(56) References Cited

U.S. PATENT DOCUMENTS

| | | | |
|---|---|---|---|
| 3,929,131 A | 12/1975 | Hardwick | 128/254 |
| 4,210,670 A | 7/1980 | Cooke | 424/324 |
| 4,230,105 A | 10/1980 | Harwood | 128/156 |
| 4,286,592 A | 9/1981 | Chandrasekaran | 128/260 |
| 4,529,601 A | 7/1985 | Broberg et al. | 514/626 |
| 4,685,911 A | 8/1987 | Konno et al. | 604/897 |
| 4,693,706 A | 9/1987 | Ennis, III | 604/87 |
| 4,747,841 A | 5/1988 | Kuratomi et al. | 604/291 |
| 4,830,855 A | 5/1989 | Stewart | 424/448 |
| 4,898,592 A | 2/1990 | Latzke et al. | 604/307 |
| 4,913,957 A | 4/1990 | Strack et al. | 428/286 |
| 4,963,360 A | 10/1990 | Argaud | 424/443 |
| 4,994,049 A | 2/1991 | Latzke et al. | 604/307 |
| 5,108,710 A | 4/1992 | Little et al. | 422/104 |
| 5,114,411 A | 5/1992 | Haber et al. | 604/203 |
| 5,128,137 A | 7/1992 | Müller et al. | 424/449 |
| 5,147,339 A | 9/1992 | Sundström | 604/307 |
| 5,152,997 A | * 10/1992 | Ebert et al. | 424/447 |
| 5,213,129 A | 5/1993 | Someah et al. | 137/101.11 |
| 5,217,718 A | 6/1993 | Colley et al. | 424/449 |
| 5,229,133 A | 7/1993 | Wright et al. | 424/473 |
| 5,276,032 A | 1/1994 | King et al. | 514/239 |
| 5,279,594 A | 1/1994 | Jackson | 604/265 |
| 5,329,976 A | 7/1994 | Haber et al. | 141/25 |
| 5,330,452 A | 7/1994 | Zook | 604/307 |
| 5,364,350 A | 11/1994 | Dittman | 604/89 |
| 5,534,021 A | 7/1996 | Dvoretzky et al. | 607/112 |
| 5,580,573 A | 12/1996 | Kydonieus et al. | 424/449 |

(List continued on next page.)

Primary Examiner—Brian L. Casler
Assistant Examiner—Catherine S. Williams
(74) Attorney, Agent, or Firm—Kirton & McConkie; Michael F. Krieger

(57) ABSTRACT

The present invention relates to a method and apparatus for increasing the delivery rate of an androgen transdermal therapeutic system through the skin. An androgen transdermal therapeutic system can be applied to a patient's skin for delivery of the androgen. A temperature modification apparatus which is capable of generating controlled heat is applied approximate to the androgen transdermal therapeutic system. The heating from the temperature modification apparatus raises the temperature of the androgen transdermal therapeutic system and raises the temperature of the patient's skin to achieve an increased rate of delivery of androgen through the skin. The controlled heat can also be used to adjust dosage rates of the androgen transdermal therapeutic system and to mimic natural circadian patterns. The controlled heating may also be used to improve or regulate the release of androgen from injected/implanted extended/controlled release systems.

58 Claims, 7 Drawing Sheets

U.S. PATENT DOCUMENTS

Figure 1:
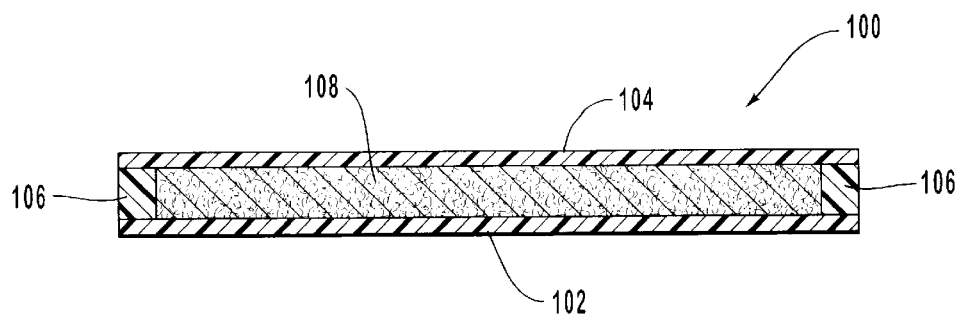

| | | | | |
|---|---|---|---|---|
| 5,605,536 A | | 2/1997 | Sibalis | 604/20 |
| 5,626,571 A | | 5/1997 | Young et al. | 604/370 |
| 5,651,768 A | | 7/1997 | Sibalis | 604/20 |
| 5,658,583 A | * | 8/1997 | Zhang et al. | 424/402 |
| 5,662,624 A | * | 9/1997 | Sundstrom et al. | 602/2 |
| 5,728,057 A | | 3/1998 | Ouellette et al. | 602/62 |
| 5,728,058 A | | 3/1998 | Ouellette et al. | 602/62 |
| 5,728,146 A | | 3/1998 | Burkett et al. | 607/109 |
| 5,733,255 A | | 3/1998 | Dinh et al. | 604/20 |
| 5,735,889 A | | 4/1998 | Burkett et al. | 607/96 |
| 5,741,318 A | | 4/1998 | Ouellette et al. | 607/108 |
| 5,837,005 A | | 11/1998 | Viltro et al. | 607/112 |
| D403,778 S | | 1/1999 | Davis et al. | D24/206 |
| D403,779 S | | 1/1999 | Davis et al. | D24/206 |
| 5,860,945 A | | 1/1999 | Cramer et al. | 602/62 |
| D407,822 S | | 4/1999 | Davis et al. | D24/206 |
| D407,824 S | | 4/1999 | Davis et al. | D24/206 |
| D408,923 S | | 4/1999 | Davis et al. | D24/206 |
| D409,757 S | | 5/1999 | Davis et al. | D24/206 |
| 5,904,710 A | | 5/1999 | Davis et al. | 607/108 |
| 5,906,637 A | | 5/1999 | Davis et al. | 607/108 |
| 5,906,830 A | | 5/1999 | Farinas et al. | 424/448 |
| 5,919,479 A | * | 7/1999 | Zhang et al. | 424/449 |
| 5,925,072 A | | 7/1999 | Cramer et al. | 607/108 |
| D412,751 S | | 8/1999 | Davis et al. | D24/206 |
| 5,955,455 A | * | 9/1999 | Labrie | 514/178 |
| D417,283 S | | 11/1999 | Davis et al. | D24/206 |
| 5,980,562 A | | 11/1999 | Ouellette et al. | 607/108 |
| 5,984,995 A | | 11/1999 | White | 75/230 |
| 6,007,837 A | * | 12/1999 | Enscore et al. | 424/449 |
| D418,606 S | | 1/2000 | Davis et al. | D24/206 |
| 6,019,782 A | | 2/2000 | Davis et al. | 607/96 |
| 6,020,040 A | | 2/2000 | Cramer et al. | 428/64.1 |
| 6,024,761 A | | 2/2000 | Barone et al. | 607/108 |
| 6,042,673 A | | 3/2000 | Johnson et al. | 156/227 |
| 6,048,326 A | | 4/2000 | Davis et al. | 602/26 |
| 6,214,374 B1 | * | 4/2001 | Schmirler et al. | 424/449 |
| 6,245,347 B1 | * | 6/2001 | Zhang et al. | 424/449 |
| 6,261,595 B1 | * | 7/2001 | Stanley et al. | 424/449 |
| 6,303,142 B1 | * | 10/2001 | Zhang et al. | 424/402 |
| 6,306,431 B1 | * | 10/2001 | Zhang et al. | 424/402 |
| 6,340,472 B1 | * | 1/2002 | Zhang et al. | 424/402 |

\* cited by examiner

METHODS AND APPARATUS FOR IMPROVED ADMINISTRATION OF TESTOSTERONE PHARMACEUTICALS

BACKGROUND

1. Field of the Invention

The present invention relates to methods and apparatus for the administration of testosterone and other androgens. More particularly, the present invention relates to using controlled heat to improve administration of testosterone pharmaceuticals.

2. Description of the Prior Art

The dermal administration of pharmaceutically active compounds involves the direct application of pharmaceutically active formulation(s) to the skin, wherein the skin absorbs a portion of the pharmaceutically active compound which is then taken up by the blood stream. Such administration has long been known in the practice of medicine and continues to be an important technique in the delivery of pharmaceutically active compounds. For example, U.S. Pat. No. 4,286,592, issued Sep. 1, 1981, to Chandrasekaran shows a bandage for administering drugs to a user's skin consisting of an impermeable backing layer, a drug reservoir layer composed of a drug and a carrier, and a contact adhesive layer by which the bandage is affixed to the skin.

For some drugs, such dermal administration offers many important advantages over other delivery techniques, such as injection, oral tablets, and capsules. These advantages include being noninvasive (thus, less risk of infection), avoiding first pass metabolism of the drug in the liver when the drug is taken orally and absorbed through the gastrointestinal tract, and improved control of the concentration of pharmaceutically active compounds in a patient's bloodstream. In particular, uncontrolled and unwanted variance in concentrations over time are typical in injection and oral administrations and are often associated with undesirable side effects and/or less than satisfactory intended effects.

In recent years there has been an increased interest in noninvasive drug delivery systems such as androgen transdermal therapeutic systems (ATTS). ATTSs offer the advantages of providing controlled release of a drug for a specified period, in contrast to the uncontrolled peaks and troughs produced by oral or parenteral application. Other advantages of these systems include: elimination of gastrointestinal absorption, reduced total dosage, less expensive than intramuscular or intravenous administration where applicable, avoidance of "first pass" inactivation by the liver, use of agents with a narrow therapeutic index, and improved compliance with decreased administration cycle.

The major goals of testosterone replacement therapy are to restore serum testosterone concentrations to within the normal range for healthy men and, if possible, in a way that mimics the normal circadian pattern of endogenous secretion. More specifically it is desirable for the therapy to mimic the natural rise of testosterone level which peaks in the morning followed by gradual decrease, reaching a valley in the evening. Use of a androgen transdermal delivery system to deliver testosterone as disclosed in the present invention in hypogonadal men can achieve this goal. Other therapeutic uses of androgen(s) with the present invention include but are not limited to treatment of hypopituitarism, osteoporosis, menstrual disorders, refractory anemia, promotion of anabolism, and influencing conditions related to puberty.

Male hypogonadism is a disorder whereby testosterone production is reduced below the normal range of 3 to 10 mg/day. Symptoms of this disorder include impairment in:libido, sexual function, energy, mood, as well as regression of secondary sex characteristics and decreases in lean body mass and bone density. Available androgen replacement modalities include intramuscular injection of long-acting testosterone esters and oral administration of alkylated and esterified testosterone. However, neither of these treatments delivers testosterone in a manner which produces plasma levels mimicking normal circadian profiles of the endogenous hormone. Recently several transdermal testosterone systems have been developed. These systems have normalized serum testosterone concentrations over a period of 24 hours and allowed some approximation of the circadian pattern seen in healthy young men. Although these systems have proven useful, they are not without side effects. For example approximately 53 percent of men experience local skin reactions (contact dermatitis) at the application sites after using Androderm®, a testosterone patch, which in some instances necessitates discontinuing use of the patch.

The term "androgen transdermal therapeutic system" or "ATTS," as used herein, is defined as an article, apparatus or method for delivery of androgen into the human body via skin permeation. An ATTS is designed for therapeutic and other uses of androgens. The term "ATTS" in this application, unless otherwise specified, only refers to those systems in which the main driving force for drug permeation is the drug concentration gradient.

The term "androgen," as used herein, is broadly defined to include any pharmaceutically active compound which is capable of regulating masculine secondary sexual characteristics, including but not limited to esters of testosterone such as propionate, phenylacetate, enanthate, cypionate, methyl testosterone, fluoxymesterone, methandrostenolone, 17 alpha-methylnortestosterone, norethandrolone, stanolone, oxymetholone, stanozolol, ethylestrenol.

Additionally, androgens include pharmaceutically active agents which promote growth, such as an increase in height and development of skeletal musculature, thickening of the skin, proliferation of sebaceous glands, as well as loss of subcutaneous fat, growth of axillary and body hair, growth of the larynx, growth of beard and initiating the onset of male pattern baldness. Androgens may also be generally described as pharmaceutical agents acting on the pituitary, testes and sebaceous glands or an agent which has nitrogen retaining anabolic effects.

The term "skin," as used herein, is defined to include stratum corneum covered skin and mucosal membranes.

In an ATTS, an androgen is usually contained in a formulation, such as a hydro-alcohol gel, and may include a rate limiting membrane between the formulation and skin for minimizing the variation in the permeation of the androgen. When an ATTS is applied to skin, the androgen begins to transport out of the formulation, and transport across the rate limiting membrane (if present). The androgen then enters the skin, enters the blood vessels and tissues under the skin, and is taken into the systemic circulation of the body by the blood. An ATTS may have certain amounts of androgen in or on the skin side (the bottom side) of the rate limiting membrane (if present) prior to use. For example, some of the drug may be present in an adhesive on the bottom side of the rate limiting membrane. In those ATTS's, that portion of the androgen on the skin side of the rate limiting membrane will enter the skin without passing through the rate limiting membrane.

After placing an ATTS on the skin, the androgen concentration in the blood typically remains unchanged from the natural levels for a period of time, before starting to gradually increase and reach a concentration deemed to be medicinally significantly beneficial, called the "therapeutic level" (the time it takes to reach the therapeutic level is referred to hereinafter as the "onset time."). The onset time and the delivery rate of the androgen into the targeted area(s) of the body for a typical ATTS are usually determined by several factors, including: the rate of release of the androgen from the formulation, the permeability of the androgen across the rate limiting membrane (if a rate limiting membrane is utilized), the permeability of the androgen across the skin (especially the stratum corneum layer), androgen storage in and release from the depot sites, the permeability of the walls of the blood vessels, and the circulation of blood and other body fluid in the tissues (including the skin) under and around the ATTS.

While an ATTS works well in many aspects, current dermal androgen delivery technology has some serious limitations, including: 1) the long onset time; 2) the skin permeability being so low that a strong permeation enhancing agent has to be used to increase skin permeability, which tends to cause serious skin irritation.

It is known that elevated temperature can increase the absorption of drugs through the skin. U.S. Pat. No. 4,898,592, issued Feb. 6, 1990, to Latzke et al., relates to a device for the application of heated transdermally absorbable active substances which include a carrier impregnated with transdermally absorbable active substance and a support. The support is a laminate made up of one or more polymeric layers and optionally includes a heat conductive element which is used for distribution of the patient's body heat such that absorption of the active substance is enhanced. U.S. Pat. No. 4,230,105, issued Oct. 28, 1980, to Harwood, discloses a bandage with a drug and a heat-generating substance, preferably intermixed, to enhance the rate of absorption of the drug by a user's skin. Separate drug and heat-generating substance layers are also disclosed. U.S. Pat. No. 4,685,911, issued Aug. 11, 1987, to Konno et al., discloses a skin patch including a drug component, and an optional heating element for melting the containing formulation if body temperature is inadequate to do so.

However, it would be advantageous to develop methods and apparatus to improve the androgen administration of ATTSs, to better accommodate various clinical needs, and to minimize side effects. For example it would be advantageous to develop a drug delivery system that can elevate skin temperature to a desired temperature range. The desired temperature range should be a range which improves the administration of the androgen, but does not significantly increase the chances of trauma to the skin due to overheating. Similarly it would be advantageous to provide elevated temperatures within a prescribed range which can be altered or adjusted within the range as needed. Having an adjustable temperature would allow a patient or caregiver greater control over the absorption rate. Furthermore it would also be advantageous to provide an elevated temperature for a controlled period of time or a desired duration. It would also be advantageous to develop a method and apparatus to allow the patient or caregiver to freely select the site on the skin where temperature is to be elevated.

SUMMARY AND OBJECTS OF THE INVENTION

The present invention relates to the methods and apparatus for improving transdermal administration of testosterone pharmaceuticals through the use of controlled heat.

In the application of an androgen transdermal therapeutic system, such as the Androderm® (testosterone transdermal system manufactured by TheraTech, Inc., the absorption of the androgen is usually determined by a number of factors including: the diffusion coefficient of androgen molecules in the drug formulation, the concentration of dissolved androgen in the formulation, the skin permeability to the androgen, androgen storage in and release from the depot sites (sites in the skin and/or sub-skin tissues in which dermally-absorbed androgen molecules are stored before being gradually released into other parts of the body), the body fluid (including blood) circulation in the skin and/or other tissue under the skin, and permeability of the walls of capillary blood vessels in the sub-skin tissues. Thus, in order to address the limitations of the current dermal androgen delivery technologies, it is desirable to have control over and have the capability to favorably influence these factors. It is believed that controlled heating can potentially favorably affect each one of the above factors for more efficient delivery of androgen.

Specifically, increased temperature generally can increase diffusion coefficients of the androgens in the formulations and their permeability across the skin. Increased heat also increases the blood and/or other body fluid flow in the tissues under the ATTS, which should carry the drug molecules into the systemic circulation at faster rates. Additionally, increased temperature also increases the permeability of the walls of the capillary blood vessels in the sub-skin tissues. Thus, the present invention uses controlled heating to affect each of the above factors for obtaining controllable dermal absorption of androgens.

Skin irritation is a major problem with ATTSs currently on the market. The skin irritation is believed to be mainly caused by a permeation enhancer in the formulation. (In the case of Androderm®, the permeation enhancer is monoglyceral oleate). The permeation enhancer is needed to increase skin permeability so that sufficient testosterone can permeate across the skin. The degree of skin irritation is usually positively correlated with the permeation enhancer concentration in the formulation and contact time with the skin. Since controlled heat can significantly increase dermal skin absorption, it is conceivable that, with controlled heat, one may be able to reduce the concentration of the enhancer in the formulation, reduce the contact time between the formulation and the skin, and/or use a milder permeation enhancer. Properly doing so should reduce skin irritation while still delivering sufficient testosterone. In other words, using controlled heat can shift at least some burden to enhance skin permeability from permeation enhancer to heat, which is a much safer way to enhance skin permeability.

This invention provides novel methods and apparatus for controlled heating (hereinafter "temperature control apparatus") during the application of the ATTS, such that heating can be initiated, maintained and terminated to accommodate the patient's needs. Through the proper selection of the moment(s) to initiate controlled heating, the heating temperature, the moment(s) to increase or decrease the temperature, and moment(s) to stop the controlled heating, the following control/manipulation of the absorption rates can be achieved: 1) the onset time of the androgen in the ATTS can be shortened; and 2) the androgen absorption rate throughout a selected period of duration or throughout the entire duration of the ATTS application can be increased.

The present invention also relates to methods and apparatus for using an insulating device, such as a cover made of insulating material (i.e. closed-cell foam tape) with adhesive edges, and a size slightly larger than the ATTS to cover the ATTS when the ATTS and the skin of the user is exposed to extreme temperature (i.e. hot shower or hot tub bath; direct sunshine).

One of the more important aspects of the present invention is the apparatus for generating and providing controlled heating. The controlled heat generating apparatus generally comprises temperature regulating mechanism such as a heat generating medium and means to pass the heat generated by the heat generating medium to the ATTS, the skin, and/or the sub-skin depot and storage sites. A controlled heat generating apparatus generally further includes a mechanism (such as tape, adhesive, and the like) for affixing the apparatus onto the ATTS and/or the skin. Preferably, the affixation mechanism securely holds the controlled heat generating apparatus in place while in use, but also allows relatively easy removal after use. Additionally, the controlled heat generating apparatus may further include a mechanism for reducing and/or terminating the generation of heat. When the heat generating apparatus is used in conjunction with an ATTS, the shape and size of the controlled heat generating apparatus may be specially made to accommodate the ATTS with which they are to be employed.

Controlled elevation of skin temperature provides specific advantages over the prior art. For example, the present invention provides elevation of skin temperature within a predetermined temperature range. In one embodiment, this predetermined temperature range is made possible by providing an oxidation reaction within a compartment having a controlled permeability to oxygen. By varying the compartment's permeability to oxygen, the temperature elevation caused by the oxidation reaction can be controlled or more precisely regulated within the predetermined narrow range. The duration of the elevated temperature can be controlled by removing the device entirely from the skin, by preventing oxygen from entering the compartment containing the oxidation reactants, or by providing a predetermined amount of oxidation reactants which will generate heat for a given amount of time when exposed to oxygen. Furthermore the heating site may be freely selected where the heating apparatus is not incorporated with the ATTS. Thus, the present invention provides controlled heating.

One embodiment of a temperature control apparatus is a shallow chamber including air impermeable side wall(s), a bottom wall, and an air impermeable top wall which has area(s) with limited and desired air permeability (e.g., holes covered with a microporous membrane or a membrane with a specific rate of permeability to oxygen). A heat generating medium is disposed within the shallow chamber. The heat generating medium preferably comprises a mixture of iron powder, activated carbon, salt, water, and, optionally, sawdust. The controlled heat generating apparatus is preferably stored in an airtight container from which it is removed prior to use. After removal from the airtight container, oxygen in the atmosphere ("ambient oxygen") flows into the heat generating medium through the areas on the air impermeable top with desired air-permeability to initiate a heat generating oxidation reaction (i.e., an exothermic reaction). The desired heating temperature and duration can be obtained by controlling the flow air through the top (e.g., selecting the right size and number of holes on the cover and/or selecting the microporous membrane covering the holes for a specific air permeability), and/or by selecting the right quantities and/or ratios of components of the heat generating medium. Air flow through the sides of the chamber may be additionally or alternatively controlled in like manner.

This embodiment of the controlled heat generating apparatus preferably includes a mechanism for affixing the controlled heat generating apparatus onto the skin or an ATTS that is applied to the skin. For applications where the removal or termination of the heating might be necessary, the heat generating apparatus may also have a mechanism for allowing easy removal from the ATTS and/or the skin or for termination of the heating. One mechanism for allowing easy removal of the heat generating apparatus from an ATTS without removing the ATTS from the skin comprises a layer of adhesive on the side walls of the heat generating apparatus with an nonadhesive area or less adhesive area (less adhesive than the adhesive affixing the ATTS to the skin) at the bottom of the shallow chamber. The non- or less adhesive area may have a shape similar to that of the ATTS. When such a heat generating apparatus is applied onto the ATTS which is on the skin, the adhesive at the bottom of the side walls of the heat generating apparatus adheres to the skin, and non- or less adhesive part is on top of, but not adhered or not strongly adhered to the ATTS. This allows for removal of the heat generating apparatus without disturbing the ATTS.

In the present invention, means for preventing heat loss is also provided. Means for preventing heat loss includes insulating materials used in the drug delivery and temperature control components. Other means for preventing heat loss include using adhesives and other means for securing and sealing the heat generating apparatus patch to the skin of the user and the ATTS so that heat does not escape through unsecured edges or corners of the drug delivery system, as well as customized shaping or molding of the heat generating apparatus patch to more appropriately fit an ATTS or a specific part of the user's body. For example, a heat generating apparatus patch may have a substantially oval shape. The oval shape facilitates the prevention of heat loss through unsecured corners by eliminating corners which may be difficult to secure and result in heat loss.

Another embodiment of the present invention provides a foam cover for the heat generating apparatus patch. The foam tape cover has insulative properties which help to prevent heat loss through the cover and which help to prevent varying ambient temperatures from adversely affecting the heat generated by the heat generating apparatus patch. Moreover, an insulative cover capable of insulating the exposed surfaces of the heat generating apparatus patch and ATTS is also contemplated.

Although one application of such a heat generating apparatus is to be used in connection with an ATTS, it is understood that the heat generating apparatus can also be applied directly to the skin to increase the release of drugs from depot sites or sites of injection or implantation of controlled released drugs (storage sites), or to accelerate the absorption of subcutaneously or intramuscularly injected androgens.

The heat generating mechanism of the present invention for the controlled heat generating apparatus is not limited to the preferred exothermic reaction mixture of iron powder, activated carbon, salt, water, and, optionally, sawdust, but may include a heating unit whose heat is generated by other exothermic chemical reactions.

Similarly, an electric heating unit may be used. The electric heating unit, preferably, includes a two dimensional surface to pass the heat to the ATTS and/or the skin. The electric heating unit may also include a temperature feedback system and temperature sensor that can be placed on the ATTS or the skin. The temperature sensor monitors the temperature at the ATTS or skin and transmits an electric signal based on the sensed temperature to a controller which regulates the electric heating unit to keep the temperature at the ATTS or skin at desired levels. Preferably, a double sided adhesive tape can be used to affix the electric heating unit onto the skin.

The heat generating mechanism may also comprise an infrared generating unit and mechanism to direct the infrared radiation onto the ATTS or the skin. It may also have a temperature feedback system and temperature sensor that can by placed on an ATTS or the skin to control the intensity of the infrared emission in order to maintain the temperature at the ATTS or skin at desired levels.

The heat generating mechanism may further comprise a microwave generation unit and a mechanism to direct the microwave radiation onto the ATTS or the skin. Again, the heat generating mechanism may have a temperature feedback system and a temperature sensor to regulate the intensity of the microwave emission to maintain the temperature at the ATTS or skin at desired levels.

It is an object of some embodiments of the present invention to provide an apparatus for increasing the diffusion coefficient of androgen molecules in drug formulations used in a transdermal drug delivery system.

It is an additional object of some embodiments of the present invention to provide a method and apparatus for increasing the skin permeability to the androgen of a transdermal drug delivery system.

It is yet another object of some embodiments of the present invention to provide a method and apparatus for manipulating the storage and release of the androgen from depot sites with controlled heat.

It is yet a further object of one embodiment of the invention to provide a method and apparatus for increasing body fluid circulation near a drug delivery site thereby increasing entrance of a drug formulation into systemic circulation with controlled heat.

It is yet an additional object of some embodiments of the present invention to provide a method and apparatus for increasing the permeability of the walls of capillary blood vessels in subskin tissues for facilitating uptake of dermally absorbed androgen into the systemic circulation.

It is still another object of some embodiments of the present invention to reduce the concentration of a permeation enhancer used in a transdermal drug delivery system and reduce contact time between the skin of a patient and the drug formulation used in a transdermal drug delivery system, particularly a system having a permeation enhancer, while still delivering a sufficient amount of androgen via skin permeation.

It is still further an object of some embodiments of the present invention to provide a method and apparatus for using a mild permeation enhancer in a transdermal drug delivery system while still delivering sufficient androgen.

It is still an additional object of one embodiment of present invention to provide a method and apparatus for shifting the burden to enhance permeability and improve performance of a transdermal drug androgen system from the permeation enhancer to heat.

It is another object of some embodiments of the present invention to provide a method and apparatus which can more closely mimic circadian patterns as they relate to androgen concentration within the blood stream.

BRIEF DESCRIPTION OF THE DRAWINGS

While the specification concludes with claims particularly pointing out and distinctly claiming that which is regarded as the present invention, the objects and advantages of this invention may be more readily ascertained from the following description of the invention, when read in conjunction with the accompanying drawings in which:

FIG. 1 is a side cross-sectional view of an embodiment of a temperature control apparatus according to the present invention;

FIG. 2 is a side cross-sectional view of another embodiment of a temperature control apparatus according to the present invention;

FIG. 3 is a side cross-sectional view of an embodiment of an androgen transdermal therapeutic system according to the present invention;

FIG. 4 is a side cross-sectional view of the temperature control apparatus of FIG. 2 in conjunction with the androgen transdermal therapeutic system of FIG. 3 according to the present invention;

FIG. 5 is a graph of temperature time versus for a temperature control apparatus according to the present invention;

FIG. 6 is a graph of skin temperature produced by a temperature control apparatus according to the present invention, as function of time;

FIG. 7 is a graph of skin temperature produced by a temperature control apparatus according to the present invention, as function of time;

FIG. 8 is a side cross-sectional view of another embodiment of a temperature control apparatus according to the present invention;

FIG. 9 is a side cross-sectional view of another embodiment of an androgen transdermal therapeutic system according to the present invention;

FIG. 10 is a side cross-sectional view of the temperature control apparatus of FIG. 8 in conjunction with the an androgen transdermal therapeutic system of FIG. 9 according to the present invention;

FIG. 11 is a side cross-sectional view of still another embodiment of an androgen transdermal therapeutic system according to the present invention;

FIG. 12 is a side cross-sectional view of the temperature control apparatus of FIG. 8 in conjunction with an androgen transdermal therapeutic system of FIG. 11 according to the present invention;

FIG. 13 is a side cross-sectional view of another embodiment of an androgen transdermal therapeutic system having a rate limiting membrane according to the present invention;

FIG. 14 is a side cross-sectional view of an electric temperature control mechanism according to the present invention;

FIG. 15 is a side cross-sectional view an insulative material over an ATTS for minimizing undesired temperature variation and/or increasing the temperature of the ATTS and the skin thereunder according to the present invention;

FIG. 16 is a cross-section of an integrated temperature control apparatus and androgen transdermal therapeutic system;

FIG. 17 is a cross-section of another embodiment of an integrated temperature control apparatus and transdermal therapeutic system.

DETAILED DESCRIPTION OF SOME PREFERRED EMBODIMENTS

FIGS. 1–17 illustrate various views of temperature control or other apparatus and an topically or regionally directed therapeutic application and related data charts. It should be understood that the figures presented in conjunction with this description are not meant to be illustrative of actual views of any particular apparatus, but are merely idealized representations which are employed to more clearly and fully depict the present invention than would otherwise be possible. Elements common between the figures retain the same numeric designations.

FIG. 1 illustrates a temperature control apparatus 100 of the present invention comprising a chamber defined by a bottom wall 102, a top wall 104, and side walls 106 wherein a temperature regulating mechanism 108 is disposed within the chamber. The temperature regulating mechanism 108 can include a heat generating oxidation reaction mechanism, electric heating unit, exothermic crystallization mechanism, endothermic crystallization mechanism, heating/cooling mechanism, cooling mechanism, or the like.

Figure 2:
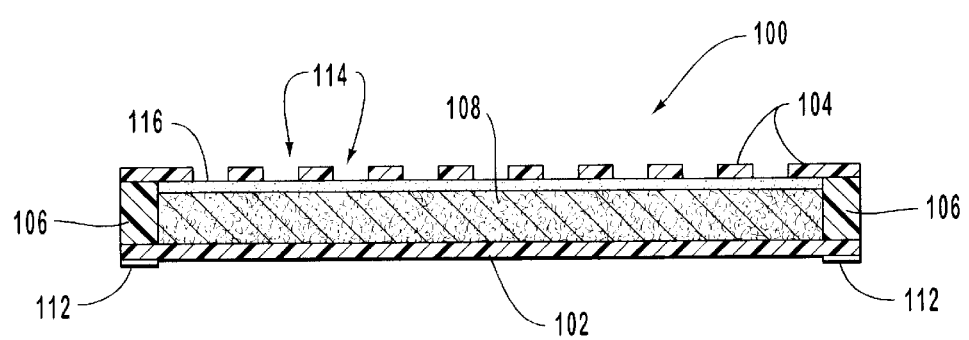

FIG. 2 illustrates a temperature control apparatus 100 comprising a temperature regulating mechanism 108 surrounded by a bottom wall 102, a top wall 104, and side walls 106. The bottom wall 102 is preferably a plastic material and the side walls 106 are preferably made of a flexible air impermeable material, such as air impermeable closed-cell foam material. A portion or all of the bottom wall 102 of the temperature control apparatus 100 includes an adhesive material 112 for attachment to an ATTS or to the skin of a patient. The temperature regulating mechanism 108 preferably comprises a composition of activated carbon, iron powder, sodium chloride and water in a proper ratio. Optionally, wood powder may be added to the composition to facilitate the airflow within the composition and/or provide "body" to the composition. The top wall 104 is preferably also a flexible air impermeable material having holes 114 therethrough. An air permeable membrane 116 is, preferably, disposed between the top wall 104 and the temperature regulating mechanism 108 to regulate the amount of air reaching the temperature regulating mechanism 108 through the holes 114. The air permeable membrane 116 is preferably a microporous film (such as No. 9711 microporous polyethylene film—CoTran™, 3M Corporation, Minneapolis, Minn., USA).

Figure 3:
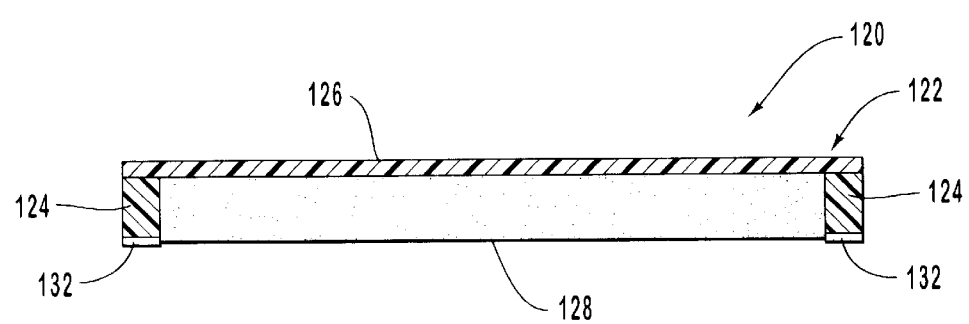

FIG. 3 illustrates a dermal drug delivery system 120 such as an androgen transdermal therapeutic system (hereinafter "ATTS 120") comprising a housing 122 made of a flexible material(s). The housing 122 preferably comprises side walls 124 and a top wall 126 with a drug formulation 128 disposed within the housing 122. Preferably, the bottom of the ATTS 120 side walls 124 include an adhesive 132 to affix the ATTS 120 to the skin of a patient.

Figure 13:
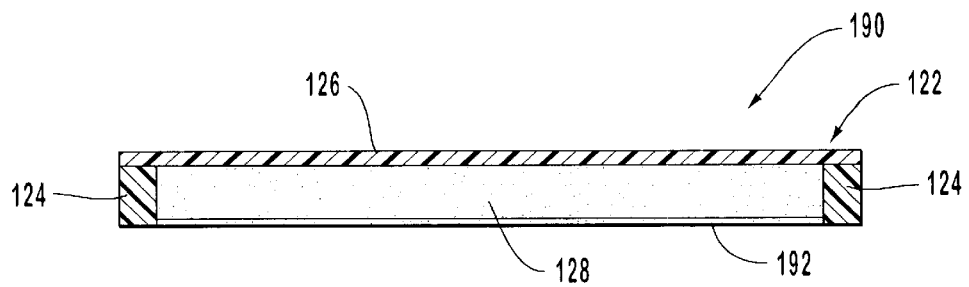

The Androderm® patch manufactured by TheraTech, Inc. is an androgen transdermal therapeutic system similar to the ATTS in FIG. 3 and FIG. 13. The Androderm® patch is capable of providing testosterone transdermally to a patient for a 24 hour period. The Androderm® system provides a drug formulation reservoir defined by a polyester ethylene vinyl acetate laminate film backing secured along its perimeter to the perimeter of a microporous polyethylene film. The two films are secured to each other in such a way as to form a drug formulation reservoir between the two films. A drug formulation containing testosterone resides in the reservoir. The microporous polyethylene film is permeable and allows the drug formulation to migrate across the microporous membrane and be absorbed into skin, when the drug reservoir is attached to the skin of the patient. When in storage, a drug formulation is prevented from crossing the microporous polyethylene film by a sealed disc of ethylene vinyl acetate copolymer film. The disc acts as a physical barrier to the migration of the drug formulation. The disc is attached to a polyester film release liner. The release liner preserves adhesive disposed on the bottom of the microporous film and the disc prevents the drug formulation from crossing the membrane while the Androderm® patch is in storage. The release liner and disc are removed prior to administration of the patch.

Figure 4:
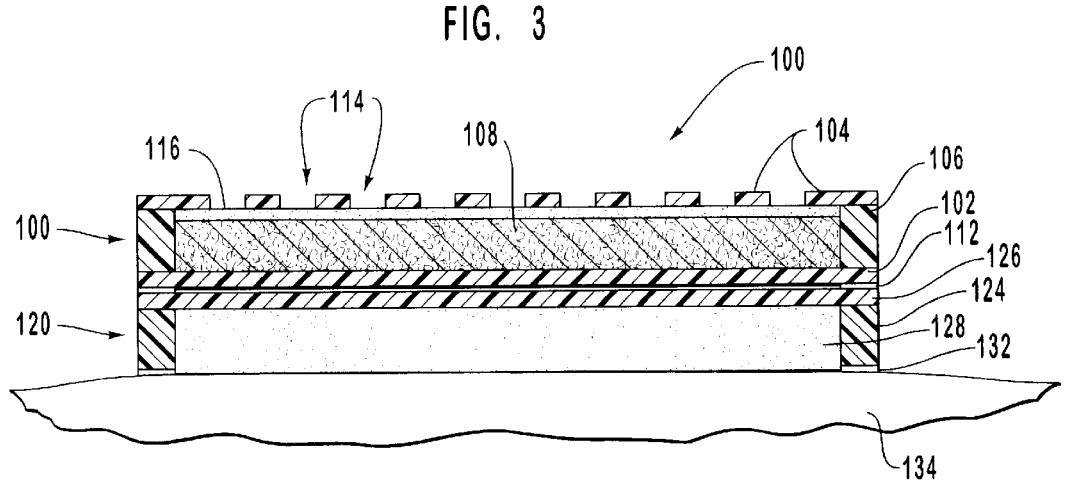

FIG. 4 illustrates the temperature control apparatus 100 of FIG. 2 attached to the ATTS 120 of FIG. 3. The ATTS 120 attaches to a portion of the skin 134 of a patient. The area of the temperature regulating mechanism 108 is preferably slightly larger than that of the drug formulation 128. The temperature control apparatus 100 and the ATTS 120 are preferably stored in separate compartments of an air tight container (or in separate air tight containers).

EXAMPLE 1

One example of using the embodiment of the present invention illustrated in FIGS. 2–4 for administering androgens consists of a patient or care giver placing the ATTS 120 on the skin 134 of the patient, ATTS 120 preferably is affixed to the skin 134 with adhesive 132. The patient or care giver then attaches the temperature control apparatus 100 on top of the ATTS 120, which adheres to the ATTS 120 with temperature control apparatus adhesive 112. Oxygen in ambient air flows into the temperature regulating mechanism 108 through holes 114 and air permeable membrane 116. Of course, it is understood that the rate at which oxygen contacts the temperature regulating mechanism 108 is determined by the size and number of the holes 114 on the top wall 104, as well as the permeability of the air permeable membrane 116. A heat generating (exothermic) chemical reaction occurs in the temperature regulating mechanism 108. Heat from this reaction passes through the temperature control apparatus bottom wall 102, through ATTS top wall 126, through the drug formulation 128, and increases the temperature of the patient's skin 134 under the ATTS 120.

In actual experimentation the temperature control apparatus 100 was a Controlled Heat-Aided Drug Delivery (CHADD) patch comprising side walls 106 defined by a 1/8 inch thick rectangular foam tape (2 layer of No. 1779 1/16" white foam tape, 3M CORPORATION, MINNEAPOLIS, MINN., USA Corporation, Minneapolis, Minn., USA) with an outer dimension of about 2.25 inches by 4 inches with an opening therein having an inner dimension of about 1.76 inches by 3.5 inches, the bottom wall 102 comprising rectangular medical tape (No. 1525L plastic medical tape, 3M Corporation, Minneapolis, Minn., USA Corporation, Minneapolis, Minn., USA) of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA Corporation, Minneapolis, Minn., USA) with forty-five holes 114 (diameters approximately 0.9 mm, in a 5 by 9 pattern with about 7.5 mm to 8.0 mm center spacing) there through. The side walls 106, the bottom wall 102, and the top wall 104 defined a chamber. The holes 114 of the top wall 104 were covered by an air permeable membrane 116 comprising a microporous membrane (No. 9711 microporous polyethylene film—CoTram™, 3M Corporation, Minneapolis, Minn., USA Corporation, Minneapolis, Minn., USA) disposed between the top wall 104 and the temperature regulating mechanism 108. The side walls 106, the bottom wall 102, and the top wall 104 all had 1/8" rounded corners. The temperature regulating mechanism 108 disposed in the chamber comprised a mixture of activated carbon (HDC grade—Novit Americas, Inc., USA) Americas, Inc., USA), iron powder (grade R1430—ISP Technologies, USA), saw dust (Wood Flour, Pine—Pioneer Sawdust, USA), sodium chloride and water in the weight ration of approximately 5:15:3:2:6 weighing approximately 16.5 grams. The heat-generating medium composed of activated carbon, iron powder, sawdust, sodium chloride powder, and water was placed in the foam tape reservoir in the CHADD patch. The CHADD patch was then placed into a heat sealable medical grade foil pouch and immediately sealed with a thermal impulse sealer. The temperature control apparatus 100 was thereby sealed in an air-tight container immediately after fabrication.

Figure 5:
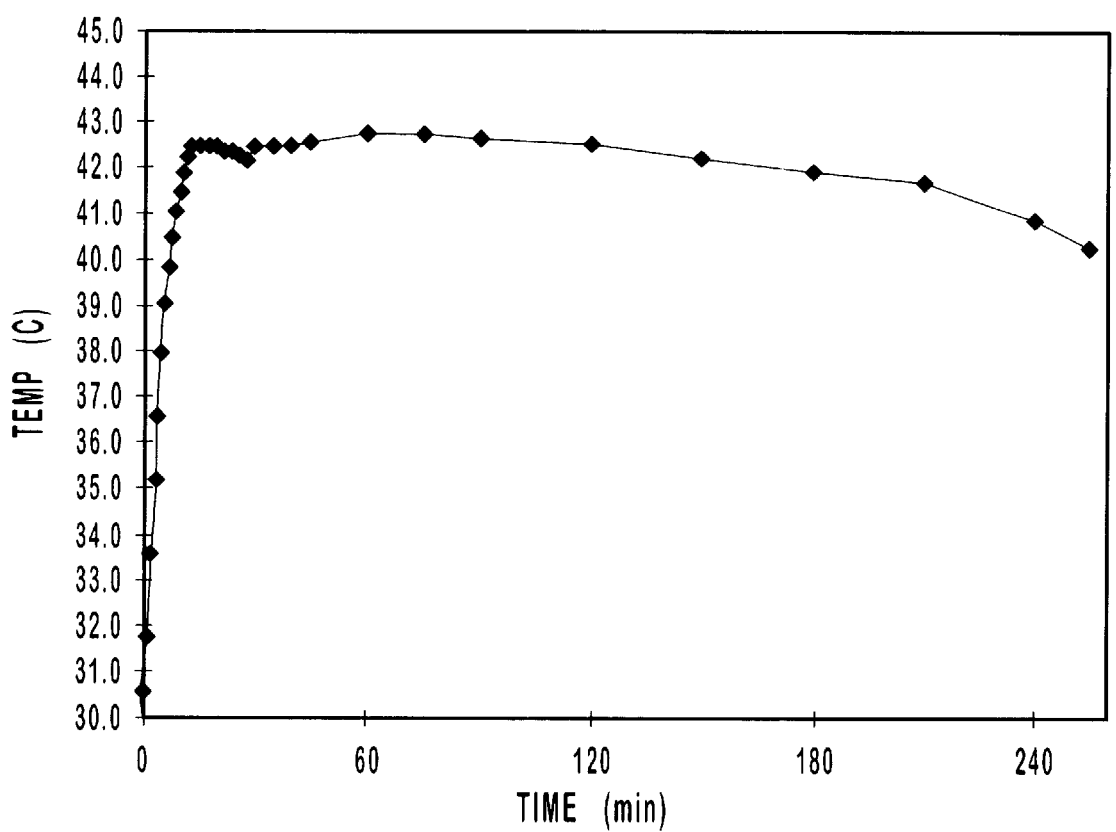

The temperature control apparatus 100 was tested on a volunteer with a temperature probe placed between the temperature control apparatus 100 and the volunteer's skin to measure the temperature. The results of this temperature experiment are illustrated in FIG. 5 and Table A which show that the temperature control apparatus 100 was capable of keeping the skin temperature to a narrow, elevated range of about 41° C. to 43° C. for extended periods of time (at least about 240 minutes).

TABLE A

| Time (minutes) | Temperature (° C.) |
| --- | --- |
| 0 | 30.6 |
| 1 | 31.8 |
| 2 | 33.6 |
| 3 | 35.2 |
| 4 | 36.6 |
| 5 | 38.0 |
| 6 | 39.1 |
| 7 | 39.9 |
| 8 | 40.5 |
| 9 | 41.1 |
| 10 | 41.5 |
| 11 | 41.9 |
| 12 | 42.3 |
| 13 | 42.5 |
| 14 | 42.5 |
| 15 | 42.5 |
| 16 | 42.5 |
| 17 | 42.5 |
| 18 | 42.5 |
| 19 | 42.5 |
| 20 | 42.5 |
| 22 | 42.4 |
| 24 | 42.4 |
| 26 | 42.3 |
| 28 | 42.2 |
| 30 | 42.5 |
| 35 | 42.5 |
| 40 | 42.6 |
| 45 | 42.6 |
| 60 | 42.5 |
| 75 | 42.8 |
| 90 | 42.7 |
| 120 | 42.6 |
| 150 | 42.3 |
| 180 | 42.0 |
| 210 | 41.8 |
| 240 | 41.0 |
| 255 | 40.4 |

In a pilot study designed to determine if heat-generated from a control heated drug delivery system would significantly increase the absorption of testosterone, one adult human volunteer received an Androderm® 5 mg patch for 12 hours in the first treatment arm and an Androderm® 5 mg patch plus a CHADD controlled heat activated dermal delivery patch for 12 hours in the second treatment arm. A period of three days separated each treatment arm. Androderm® patches were produced by TheraTech, Inc., Salt Lake City, Utah, USA. The CHADD patch was manufactured by ZARS, Inc., and was similar in function and design to the heating patch used to generate the data of Table D (below). It was composed of five components; a foam tape cover, microporous membrane, a heat-generating medium, a foam tape reservoir, into which the heat-generating medium was placed, and a bottom adhesive tape layer. Except for the heat-generating medium, 3M Corporation, Minneapolis, Minn., USA drug delivery systems manufactures all the materials used in the CHADD patch components.

Venous blood samples for serum testosterone concentration were obtained prior to the patch application (zero hours), and at 2, 4, 6, 8, 10 and 12 hours following patch application. After completing the blood draw at 12 hours, the patch system was removed. The Androderm® testosterone transdermal system which was selected was a 5 mg system having a total contact surface area of 24 $cm^2$ with a 15 $cm^2$ drug reservoir containing 24.3 mg testosterone USP dissolved in an alcohol-based gel. Serum testosterone concentrations were determined using a radioimmunoassay. Table B illustrates the serum testosterone concentrations at 0, 2, 4, 6, 8, and 10 hours. It was found that the administration of testosterone using an androgen testosterone transdermal system with a controlled heat aided drug delivery patch produced significantly higher testosterone concentrations in the subject's blood than using an Androderm® testosterone transdermal system patch alone.

TABLE B

Serum Testosterone Concentrations

| Time (hour) | Testosterone Concentration (ng/DL) Androderm ® Patch | Testosterone Concentration (ng/DL) Androderm ® + CHADD Patch |
| --- | --- | --- |
| 0 | 340 | 325 |
| 2 | 456 | 722 |
| 4 | 402 | 961 |
| 6 | 567 | 1020 |
| 8 | 339 | 558 |
| 10 | 463 | 647 |

Thus, it is believed that the increased temperature increases the skin permeability (compared with an ATTS 120 without such a heating mechanism), which results in the testosterone entering the patient's systemic circulation faster. This should result in serum testosterone concentrations reaching desired therapeutic levels more quickly. The heating is also believed to increase the body fluid circulation and blood vessel wall permeability in the sub-skin tissues, and cause testosterone to spend less time in the sub-skin depot site. As a result, the patient receives the androgen compound more quickly and may receive improved treatment (in a situation where ATTS 120 without heating does not deliver a sufficient amount of testosterone.).

It is understood that the desired increase in androgen concentration in the systemic circulation may be an increase in the concentration of the androgen delivered by the delivery system, and/or a derivative of the androgen delivered by the delivery system and/or a different androgen. For example, testosterone enanthate may be delivered by a delivery system in order to increase the concentration of testosterone in systemic circulation. Thus, the delivery system androgen (in this case testosterone enanthate) facilitates an increase in the concentration of the target androgen (testosterone) in the systemic circulation.

In a second study designed to determine if heat generated from a control heated drug delivery system would significantly increase the absorption of testosterone, serum testosterone levels of six adult human volunteers were taken over a twelve hour period. Then the volunteers received an Androderm® 5 mg patch for 12 hours in a first treatment arm. Later, the volunteers received an Androderm® 5 mg patch plus a CHADD controlled heat activated dermal delivery patch for 12 hours in a second treatment arm. A period of three days separated each treatment arm. The Androderm® patches were produced by TheraTech, Inc., Salt Lake City, Utah, USA. The CHADD patches was manufactured by ZARS, Inc., and were similar in function and design to the heating patch used to generate the data of Table D (below). It was composed of five components; a foam tape cover, microporous membrane, a heat-generating medium, a foam tape reservoir, into which the heat-generating medium was placed, and a bottom adhesive:tape layer. Except for the heat-generating medium, 3M Corporation, Minneapolis, Minn., USA drug delivery systems manufactures all the materials used in the CHADD patch components. Gauze tape was placed between the CHADD patch and Androderm patch to facilitate the removal of the CHADD patch after it was used.

Venous blood samples for serum testosterone concentration were obtained in the non-treatment arm at 0, 1, 2, 4, 6, 8, 10 and 12 hours to establish base line data. Venous blood samples for serum testosterone concentration were obtained prior to the patch application (zero hours), and at 1, 2, 4, 6, 8, 10 and 12 hours following patch application. After completing the blood draw at 12 hours, the patch system was removed. The Androderm® testosterone transdermal system which was selected was a 5 mg system having a total contact surface area of 24 cm$^2$ with a 15 cm$^2$ drug reservoir containing 24.3 mg testosterone USP dissolved in an alcohol-based gel. Serum testosterone concentrations were determined using a radioimmunoassay. Table B-1 illustrates the serum testosterone concentrations at 0, 1, 2, 3, 4, 6, 8, 10, and 12 hours. As with the pilot study, this study showed that the administration of testosterone using an androgen testosterone transdermal system with a controlled heat aided drug delivery patch produced significantly higher testosterone concentrations in the subject's blood than using an Androderm® testosterone transdermal system patch alone.

TABLE B-1

CHADD-Androderm study 5/99

Serum Testosterone conc. (ng/DL)

| Time (hr) | Natural baseline | Androderm alone | Androderm + CHADD | Andro-base | Andro + CHADD-base |
|---|---|---|---|---|---|
| Subject #1 | | | | | |
| 0 | 500 | 515 | 354 | 15 | -146 |
| 1 | 425 | 442 | 566 | 17 | 141 |
| 2 | 464 | 429 | 626 | -35 | 162 |
| 4 | 542 | 687 | 967 | 145 | 425 |
| 6 | 567 | 470 | 706 | -97 | 139 |
| 8 | 353 | 498 | 735 | 145 | 382 |
| 10 | 315 | 506 | 742 | 191 | 427 |
| 12 | 388 | 614 | 727 | 226 | 339 |
| Subject #2 | | | | | |
| 0 | 299 | 287 | 314 | -12 | 15 |
| 1 | 357 | 314 | 400 | -43 | 43 |
| 2 | 335 | 321 | 544 | -14 | 209 |
| 4 | 387 | 459 | 1020 | 72 | 633 |
| 6 | 350 | 561 | 641 | 211 | 291 |
| 8 | 397 | 509 | 555 | 112 | 158 |
| 10 | 408 | 519 | 536 | 111 | 128 |
| 12 | 335 | 523 | 597 | 188 | 262 |

TABLE B-1-continued

CHADD-Androderm study 5/99

| | | | | | |
|---|---|---|---|---|---|
| Subject #3 | | | | | |
| 0 | 360 | 394 | 414 | 34 | 54 |
| 1 | 319 | 413 | 530 | 94 | 211 |
| 2 | 271 | 455 | 666 | 184 | 395 |
| 4 | 362 | 604 | 878 | 242 | 516 |
| 6 | 389 | 677 | 590 | 288 | 201 |
| 8 | 234 | 551 | 597 | 317 | 363 |
| 10 | 295 | 588 | 542 | 293 | 247 |
| 12 | 327 | 635 | 658 | 308 | 331 |
| Subject #4 | | | | | |
| 0 | 279 | 272 | 246 | -7 | -33 |
| 1 | 285 | 241 | 441 | -44 | 156 |
| 2 | 243 | 341 | 514 | 98 | 271 |
| 4 | 214 | 322 | 592 | 108 | 378 |
| 6 | 261 | 394 | 586 | 133 | 325 |
| 8 | 268 | 380 | 587 | 112 | 319 |
| 10 | 240 | 393 | 456 | 153 | 216 |
| 12 | 205 | 363 | 477 | 158 | 272 |
| Subject #5 | | | | | |
| 0 | 373 | 266 | 434 | -107 | 61 |
| 1 | 370 | 409 | 567 | 39 | 197 |
| 2 | 419 | 502 | 847 | 83 | 428 |
| 4 | 314 | 667 | 1103 | 353 | 789 |
| 6 | 364 | 732 | 790 | 368 | 426 |
| 8 | 283 | 749 | 876 | 466 | 593 |
| 10 | 356 | 650 | 723 | 294 | 367 |
| 12 | 413 | 619 | 808 | 206 | 395 |
| Subject #6 | | | | | |
| 0 | 484 | 484 | 447 | 0 | -37 |
| 1 | 457 | 518 | 864 | 61 | 407 |
| 2 | 396 | 523 | 1057 | 127 | 661 |
| 4 | 385 | 742 | 857 | 357 | 472 |
| 6 | 395 | 608 | 1076 | 213 | 681 |
| 8 | 472 | 708 | 790 | 236 | 318 |
| 10 | 420 | 528 | 787 | 108 | 367 |
| 12 | 368 | 580 | 828 | 212 | 460 |

Means

| Time (hr) | mean baseline | mean andro alone | mean andro + CHADD | mean andro-base | mean andro + CHADD-base |
|---|---|---|---|---|---|
| 0 | 382.5 | 369.67 | 368.17 | -12.83 | -14.33 |
| 1 | 368.83 | 389.5 | 561.33 | 20.67 | 192.5 |
| 2 | 354.67 | 428.5 | 709 | 73.83 | 354.33 |
| 4 | 367.33 | 580.17 | 902.83 | 212.83 | 535.5 |
| 6 | 387.67 | 573.67 | 731.5 | 186 | 343.83 |
| 8 | 334.5 | 565.83 | 690 | 231.33 | 355.5 |
| 10 | 339 | 530.67 | 631 | 191.67 | 292 |
| 12 | 339.33 | 555.67 | 682.5 | 216.3 | 343.17 |

In yet another experiment, the temperature control apparatus 100 comprised the side walls 106 defined by a ³⁄₁₆ inch thick rectangular foam tape (3 layers of No. 1779 ¹⁄₁₆" white foam tape, 3M Corporation, Minneapolis, Minn., USA Corporation, Minneapolis, Minn., USA) with an outer dimension of about 2.25 inches by 4 inches with an opening therein having an inner dimension of about 1.75 by 3.5 inches, the bottom wall 102 comprising rectangular medical tape (No. 1525L plastic medical tape, 3M Corporation, Minneapolis, Minn., USA Corporation, Minneapolis, Minn., USA) of a dimension of about 2.25 inches by 4 inches with a non-adhesive side attached to the bottom of the side walls 106, and a top wall 104 comprising a rectangular ¹⁄₃₂ inch thick foam tape (No. 9773 ¹⁄₃₂" tan foam tape, 3M Corporation, Minneapolis, Minn., USA Corporation, Minneapolis, Minn., USA) with seventy-eight holes 114 there through (diameters approximately ¹⁄₃₂ inch, in a 6 by 13 pattern with about a 6 mm center spacing). The side walls 106, the bottom wall 102, and the top wall 104 defined a chamber. The holes 114 of the top wall 104 were covered by an air permeable membrane 116 comprising a microporous membrane (no. 9711 CoTran™ membrane, 3M Corporation, Minneapolis, Minn., USA Corporation, Minneapolis, Minn., USA) disposed between the top wall 104 and the temperature regulating mechanism 108. The temperature regulating mechanism 108 disposed in the chamber comprised a mixture of activated carbon, iron powder, saw dust, sodium chloride and water in the weight ratio of approximately 5:15:3:2:6 weighing approximately 25 grams.

Figure 6:
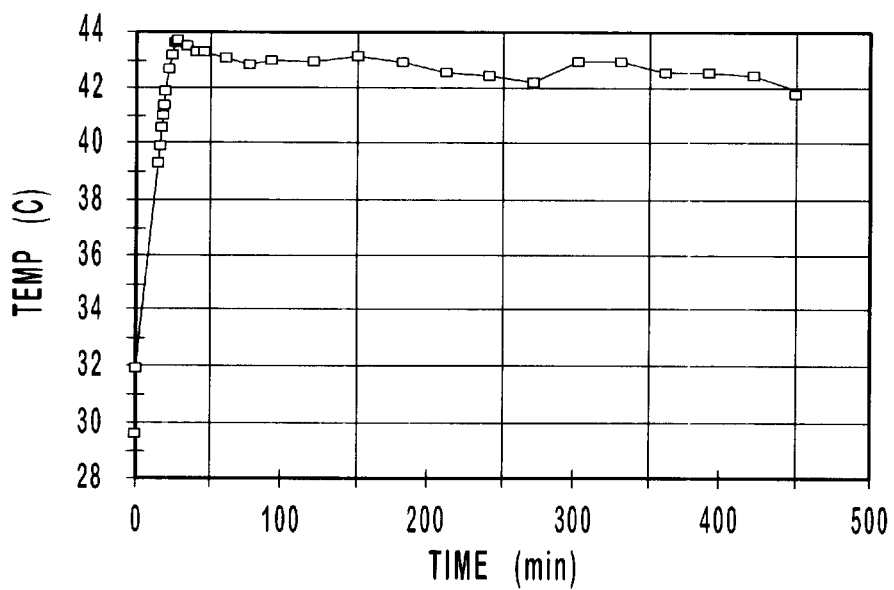

This temperature control apparatus 100 was tested on a volunteer's skin with a temperature probe placed between the temperature control apparatus 100 and the volunteer's skin to measure the temperature. The results of this temperature experiment are illustrated in FIG. 6 and Table C, which shows that the temperature control apparatus 100 was capable of keeping the skin temperature to within a narrow, elevated range of about 41 and 44° C. for extended periods of time (at least 450 minutes).

TABLE C

| Time (minutes) | Temperature (° C.) |
| --- | --- |
| 0 | 29.6 |
| 1 | 31.9 |
| 15 | 39.3 |
| 16 | 39.3 |
| 17 | 40.6 |
| 18 | 41.0 |
| 19 | 41.4 |
| 20 | 41.9 |
| 22 | 42.7 |
| 24 | 43.2 |
| 26 | 43.6 |
| 28 | 43.7 |
| 30 | 43.5 |
| 35 | 43.5 |
| 40 | 43.3 |
| 45 | 43.3 |
| 60 | 43.1 |
| 75 | 42.9 |
| 90 | 43.0 |
| 120 | 43.0 |
| 150 | 43.2 |
| 180 | 43.0 |
| 210 | 42.6 |
| 240 | 42.5 |
| 270 | 42.3 |
| 270 | 42.3 |
| 300 | 43.0 |
| 330 | 43.0 |
| 360 | 42.6 |
| 390 | 42.6 |
| 420 | 42.5 |
| 450 | 41.9 |

In a third experiment, the temperature control apparatus 100 comprised the side walls 106 defined by a ¼ inch thick rectangular foam tape (4 layers of No. 1779 1/16" white foam tape, 3M Corporation, Minneapolis, Minn., USA Corporation, Minneapolis, Minn., USA) with an outer dimension of about 2.25 inches by 4 inches with an opening therein inner dimension of about 1.75 by 3.5 inches, the bottom wall 102 comprising rectangular medical tape (No. 1525L plastic medical tape, 3M Corporation, Minneapolis, Minn., USA Corporation, Minneapolis, Minn., USA) of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA Corporation, Minneapolis, Minn., USA) with thirty-two holes 114 there through (diameters approximately 1/16 inch). The side walls 106, the bottom wall 102, and the top wall 104 defined a chamber. The holes 114 of the top wall 104 were covered by an air permeable membrane 116 comprising a microporous membrane (no. 9711 CoTran™ membrane, 3M Corporation, Minneapolis, Minn., USA Corporation, Minneapolis, Minn., USA) disposed between the top wall 104 and the temperature regulating mechanism 108. The temperature regulating mechanism 108 disposed in the chamber comprised a mixture of activated carbon, iron powder, saw dust, sodium chloride and water in the weight ratio of approximately 5:21:3:2:6 weighing approximately 31 grams.

Figure 7:
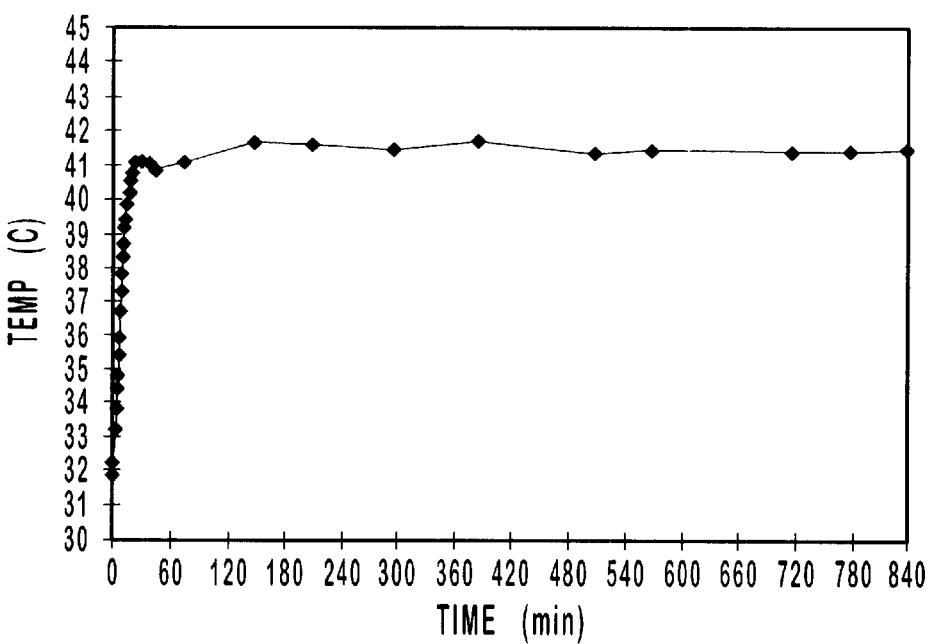

This temperature control apparatus 100 was tested on a volunteer's skin with a temperature probe placed between the temperature control apparatus 100 and the volunteer's skin to measure the temperature. The results of this temperature experiment are illustrated in FIG. 7 and Table D, which shows that the temperature control apparatus 100 was capable of keeping the skin temperature to a narrow, elevated range between about 41 and 44° C. for extended periods of time (at least 840 minutes).

TABLE D

| Time (minutes) | Temperature (° C.) |
| --- | --- |
| 0 | 31.9 |
| 1 | 32.2 |
| 2 | |
| 3 | 33.2 |
| 4 | 33.8 |
| 5 | 34.4 |
| 6 | 34.8 |
| 7 | 35.8 |
| 8 | 35.9 |
| 9 | 36.7 |
| 10 | 37.3 |
| 11 | 37.8 |
| 12 | 38.4 |
| 13 | 38.7 |
| 14 | 39.2 |
| 15 | 39.4 |
| 16 | 39.8 |
| 17 | 39.9 |
| 18 | 40.1 |
| 19 | 40.3 |
| 20 | 40.5 |
| 22 | 40.8 |
| 24 | 40.9 |
| 26 | 41 |
| 28 | 41.1 |
| 30 | 41.1 |
| 35 | 41 |
| 40 | 41 |
| 45 | 40.9 |
| 75 | 41.1 |
| 150 | 41.7 |
| 210 | 41.6 |
| 300 | 41.5 |
| 390 | 41.7 |
| 510 | 41.4 |
| 570 | 41.5 |
| 720 | 41.4 |
| 780 | 41.4 |
| 840 | 41.5 |

The results of the experiments noted above and the description of the CHADD patch offered herein indicate the CHADD patch provides unique advantages over the prior art and in some circumstances, over other methods of generating heat in a temperature control apparatus. The CHADD patch provides a safe means whereby the skin temperature can be elevated. Because the heat generating element is a controlled oxidation reaction between iron powder and oxygen, the chances of the heat generating element over heating and causing trauma to the skin are greatly reduced. Using a cover with selected air flow rate to limit the amount of oxygen reacting with the iron powder, the heat generated by the exothermic reaction can be maintained within a safe range of temperatures. Furthermore the heat generating element does not contain dangerous chemicals. Because the reactants are in powder form, they are less likely to leak if the compartment holding the reaction components is punctured, as would be the case if the components were primarily liquid.

The CHADD patch is also convenient to use. Because the CHADD patch is designed to have a selectively permeable barrier between the oxidation reactants and ambient oxygen, it is possible to vary and adjust the temperature being generated by the oxidation reaction within the compartment. This can be done by changing the number and/or size of the holes on the cover. One embodiment of the present invention provides air impermeable air hole coverings for the air holes on the cover. The user can selectively cover and uncover one or several holes to increase or decrease the rate of the exothermic reaction and thereby adjust and regulate the heat produced by the heat generating element. Alternatively, where the exposed surface area of an air permeable membrane significantly determines the rate that oxygen reacts with the heat generating element, a desired portion of the exposed surface area may be covered to regulate the temperature within the narrow range of temperatures available.

The duration of the heat can be varied by adjusting the time of the exposure of the reactants to oxygen and/or by adjusting the amount of the reactant that is placed within the compartment. The CHADD patch's capacity to be adjusted allows the CHADD patch to be used in a variety of ways to meet the needs of the patient or caregiver. Another convenient feature of the CHADD patch is its use of oxygen to activate the heat generating element. The CHADD patch is conveniently activated by simply exposing the CHADD patch to ambient oxygen, such as when the CHADD patch is taken out of its air tight pouch prior to application. The CHADD patch does not require an electric or other external power source to generate heat and thus is conveniently portable.

The CHADD patch is also unique in that it provides a low cost solution to the need for controlled heat in transdermal drug delivery. Manufacture of the CHADD patch is not unduly complex and the design and form of the CHADD patch make distribution and storage of the CHADD patch easy. The components for making the CHADD patch are readily obtained from established sources within the industry at a relatively low cost. The CHADD patch is also environmentally friendly.

Figure 8:
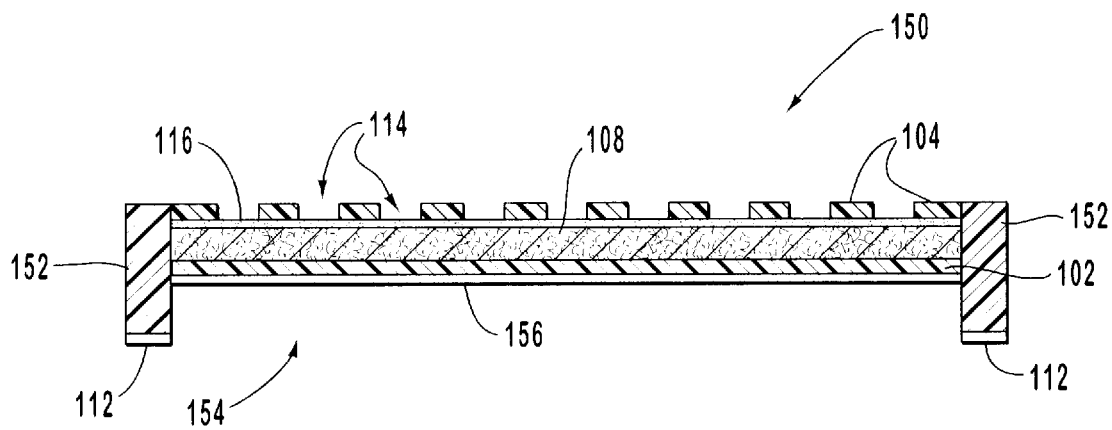

FIG. 8 illustrates another embodiment of a temperature control apparatus 150 comprising a temperature regulating mechanism 108 surrounded by a bottom wall 102, a top wall 104, and side walls 152. The side walls 152 extend a distance below the bottom wall 102 to define a cavity 154. The bottom wall 102 is preferably made of a plastic tape material and the side walls 152 are preferably made of a flexible air impermeable material, such closed-cell foam material. A portion of the bottom of the temperature control apparatus 150 includes an adhesive material 112 on the bottom of the side walls 152, and preferably, includes a second adhesive material 156 in the bottom of the bottom wall 102, wherein the second adhesive material 156 is preferably less adhesive than the adhesive material 112. Again, the temperature regulating mechanism 108 preferably comprises a composition of activated carbon, iron powder, wood powder (optional), sodium chloride, and water having a weight ratio of about 5:15:3:2:6. The iron powder may have a weigh ratio within the range of about 10 to about 30. The top wall 104 is preferably also a flexible air impermeable material having holes 114 therethrough. An air permeable membrane 116 is disposed between the top wall 104 and the temperature regulating mechanism 108 to regulate the amount of air reaching the temperature regulating mechanism 108 through the holes 114.

Figure 9:
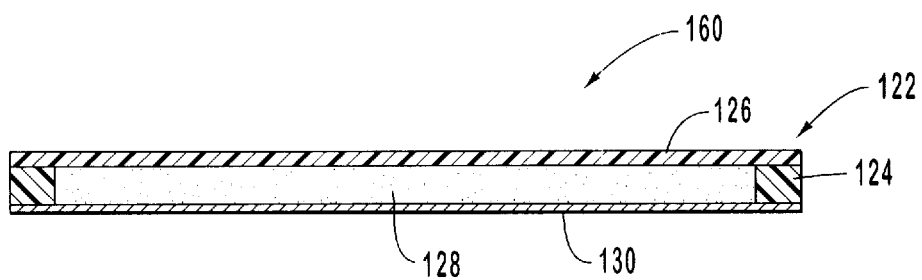

FIG. 9 illustrates an ATTS 160 comprising a housing 122 made of flexible materials. The housing 122 preferably comprises side walls 124 and a top wall 126 with a drug formulation 128 disposed within the housing 122, and may include a membrane 130 which may be a rate-limiting membrane.

Figure 10:
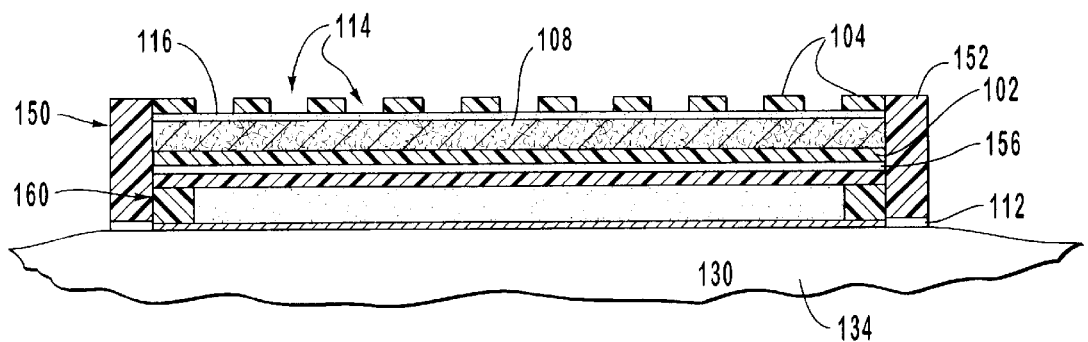

FIG. 10 illustrates the temperature control apparatus 150 of FIG. 8 attached to the ATTS 160 of FIG. 9. The ATTS 160 is placed on (or attached with an adhesive, not shown) a portion of the skin 134 of a patient and the temperature control apparatus 150 is placed over the ATTS 160, such that the ATTS 160 resides within the cavity 154 (FIG. 8). The adhesive material 112 attaches to the skin 134 and holds the temperature control apparatus 150 in place. If the ATTS 160 is not attached to the skin 134, the temperature control apparatus 150 holds the ATTS 160 in place. Preferably, the ATTS 160 is attached to the skin 134 with an adhesive material (not shown) with the temperature control apparatus 150 placed over the ATTS 160. The temperature control apparatus 150 is attached to the skin 134 with the adhesive material 112 and the second adhesive material 156 (less adhesive than any attachment adhesive (not shown) between the ATTS 160 and the skin 134 and less adhesive than the adhesive material 112 between the temperature control apparatus 150 and the skin 134) attaches the temperature control apparatus 150 to the ATTS 160. Such an arrangement results in secure adhesion of the temperature control apparatus 150 and the ATTS 160 to the skin 134, yet allows for the removal for the temperature control apparatus 150 without removing the ATTS 160.

Figure 11:
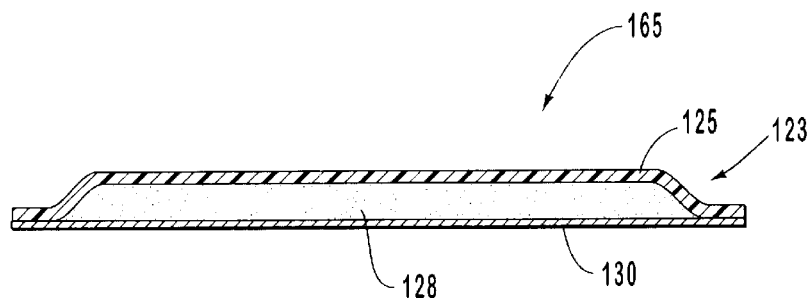

FIG. 11 illustrates an alternate ATTS 165 comprising a housing 123 made of flexible material(s). The housing 123 preferably comprises top wall 125 and a membrane 130, which may be a rate-limiting membrane, with a drug formulation 128 disposed within the housing 123.

Figure 12:
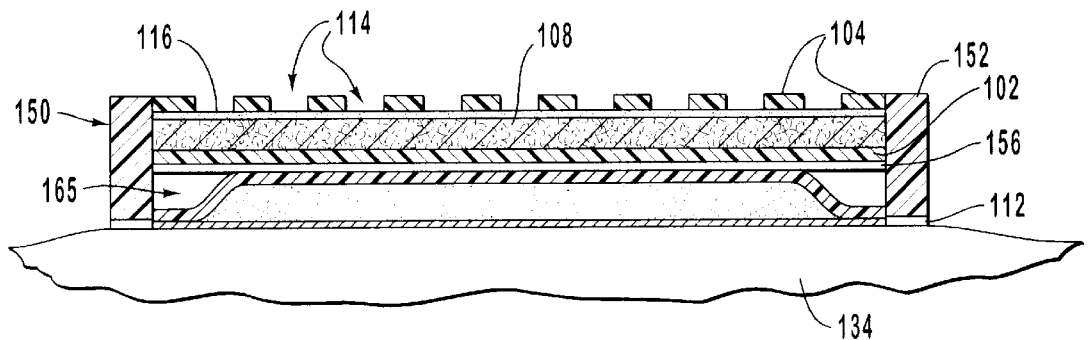

FIG. 12 illustrates the temperature control apparatus 150 of FIG. 8 attached to ATTS 165 of FIG. 11, similar to that described in FIG. 10.

EXAMPLE 2

Another example of using the embodiment of the present invention illustrated in FIGS. 8–12 for dermally administering testosterone to increase and optimize the amount of drug delivered consists of a user placing ATTS 160, 165, such as a once a day dermal testosterone patch, for example Androderm® produced by Theratech, Inc. of Salt Lake City, Utah, USA, on the skin 134. The ATTS 160, 165 is generally applied to the skin 134 at night, for example at 10 PM. The user puts the temperature control apparatus 150 on top of the ATTS 160, 165 first thing next morning. The increased temperature in the ATTS 160, 165, the skin 134 and tissues under the skin significantly increase the dermal absorption of testosterone to achieve increased delivery rates for the drug time. In addition, the ATTS 160, 165 a has permeation enhancer, such as glycerol monooleate. In a testosterone ATTS 160, a permeation enhancer is usually necessary for delivering sufficient testosterone, however, permeation enhancers such as glycerol monooleate used in Androderm® may cause serious skin irritation. With potentially less risk of irritation, the increased absorption of testosterone offered by the controlled heating may allow the reduction of the concentration of permeation enhancer which is used in the ATTS 160, 165. The heat should also make the enhancer permeate the skin faster, thus making it more effective. The ultimate result of controlled heat is that the user gets sufficient testosterone from ATTS 160, 165 when it is most needed, during the day time.

EXAMPLE 3

Yet another example of using the embodiment of the present invention illustrated in FIGS. 8–12 comprises using the temperature control apparatus 150 for administering androgen material when an increased absorption rate is desirable, such as when the diffusion coefficient of the active ingredients in the formulation 128 and/or permeability coefficient across a rate limiting membrane 130 is so low that it dominantly determines the overall absorption rate of androgen of androgen material from the ATTS 160, 165 into a patient's body. By way of example, with the use of an ATTS 160, 165 having a rate limiting membrane 130, the patient or care giver places ATTS 160, 165 on the skin 134 of the patient. If after a time of wearing the ATTS 160, 165 it is determined that, for this particular patient and for his conditions, a higher concentration of testosterone in the bloodstream is required to properly treat his condition, the temperature control apparatus 150 is placed on top of the ATTS 160, 165 to heat the ATTS 160, 165.

The increased temperature increases the diffusion coefficient of the active ingredient in the formulation in the ATTS 160, 165 and the permeability coefficient across a rate limiting membrane, thus increasing, the overall rates at which the active ingredient enters the patient's body. This, in turn, increases the concentration of active ingredient in the bloodstream. As a result, the patient gets the increased and proper effect.

EXAMPLE 4

Still another example of using the embodiment of the present invention illustrated in FIGS. 8–12 comprises using the temperature control apparatus 150 for increasing absorption rate and decreasing onset time of an androgen material from the ATTS 160, 165. By way of example with the use of a commercially available testosterone patch, such as Androderm-50®, as the ATTS 160, 165, the patient or care giver places the ATTS 160, 165 on the skin 134 of the patient and places the temperature control apparatus 150 over the ATTS 160. Preferably, the temperature control apparatus 150 includes a sufficient amount of heat generating medium for temperature regulating mechanism 108 to sustain an exothermic reaction for at least four hours.

The heat from the temperature control apparatus 150 increases the temperature at a contact surface of the skin 134 and the ATTS 160, 165 to a narrow temperature range between about 38° C. and 45° C., preferably between about 39° C. and 43° C., more preferably about 42° C. and maintains this temperature for a period of time (i.e., approximately four hours). During this time, the heat increases the speed of testosterone release from the ATTS 160, 165, the permeation rate across the skin 134, and the speed of blood circulation which carries testosterone into the systemic circulation faster. After the exothermic reaction ceases (approximately four hours), the testosterone absorption and concentration in the bloodstream begins to decrease from the elevated levels caused by the heat from the ATTS 160, 165 returns to normal (unheated) levels. The patient continues to wear the system for the next 24 hours. Compared with ATTS 160, 165 without the use of the temperature control apparatus 150, the testosterone begins to appear in the bloodstream significantly earlier to yield a shortened onset time and the testosterone concentrations in the bloodstream in the early hours of application are significantly higher than that produced by an unheated ATTS 160, 165. As a result, high serum testosterone levels are achieved in earlier hours (i.e. 4–6 hours after application first thing in the morning).

EXAMPLE 5

FIG. 13 illustrates a dermal drug delivery system 190 (hereinafter "ATTS 190") having a rate limiting membrane 192. The structure of ATTS 190 is similar to that of FIG. 3. However, the ATTS 190 includes a rate limiting membrane 192 which resides between the drug formulation 128 and the skin 134 of a patient.

Generally, the permeability of the drug in the drug formulation 128 through the rate limiting member 192 is significantly lower than the permeability of the drug in the drug formulation 128 into the skin of an average patient. Rate limiting membranes 192 are used to regulate the amount of drug delivered to the patient so that overdosing does not occur. Another aspect of the present invention is the use of a temperature sensitive rate limiting membrane, such that the drug permeation rate through the rate limiting membrane increases significantly with increasing temperature. With such an ATTS 190, the above discussed temperature control apparatus 100 (FIGS. 1 & 2) and 150 (FIG. 8), can be used to increase the drug delivery rate across the limiting membrane 192 to reduce onset time, increase steady state delivery rate, or other advantages discussed above.

Figure 14:
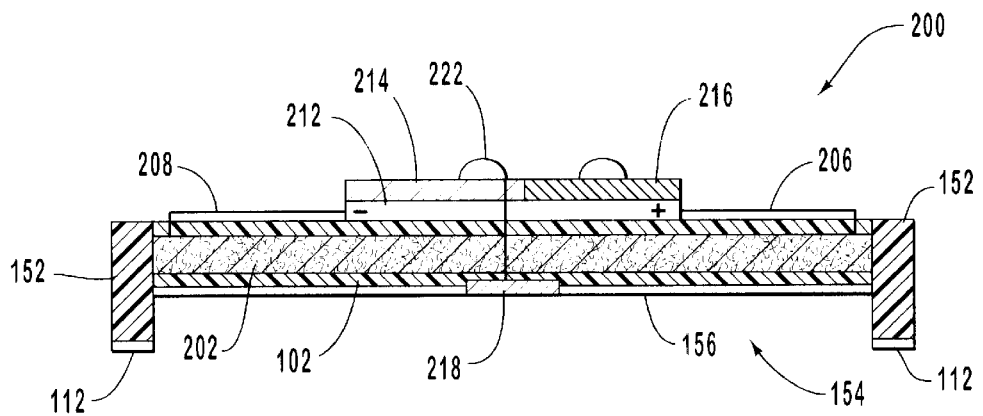

The possible temperature control apparatus are not limited to the exothermic reaction mixture of iron powder, activated carbon, salt, water, and sawdust, as discussed above. FIG. 14 illustrates an electric temperature control apparatus 200 comprising an electric heating element 202 surrounded by a bottom wall 102, a top wall 104, and side walls 152 (similar to FIG. 8). The side walls 152, preferably, extend a distance below the bottom wall 102 to define a cavity 154. It is, of course, understood that the electric heating element 202 need not have side walls 152 forming a cavity 154.

The bottom wall 102 and the side walls 152 are preferably made of a flexible air impermeable material, such as closed-cell foam material. A portion of the bottom of the temperature control apparatus 200 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. The electric heating element 202 is a heat generating medium and preferably comprises a flexible resistor plate that can generate heat when supplied with an electric current through traces 206, 208. The electric current is preferably supplied from a battery 212 attached to a control mechanism 214, and the electronic switch 216 are preferably attached to the top surface of the top wall 104. The electric heating element 202 is activated by triggering the electronic switch 216 which begins the flow of electric current from the battery 212 to the electric heating element 202. A temperature sensor 218, such as a thermistor, is preferably attached to the bottom of the bottom wall 102 and sends a signal (corresponding to the temperature at the bottom of the bottom wall 102) through electric trace 222 to the control mechanism 214. The control mechanism 214 regulates the flow of current to the electric heating element 202, so that the electric heating element 202 quickly brings the temperature at a contact surface between the bottom wall 102 and a top of an ATTS (not shown) to a predetermined level and maintains the temperature at the predetermined level. The initiation, termination and heating temperature may be similar to that in previous examples, or may be chosen by the physician based on the individual patient's need.

EXAMPLE 6

An example of storage site absorption using the embodiment of the present invention illustrated in FIGS. 1 and 2 consists of a patient or care giver injecting an androgen in controlled extended release formulation under the skin surface. By way of example, a controlled release formulation of androgen may comprise an androgen, such as testosterone, testosterone enanthate or cypionate which is incorporated into a controlled release drug delivery system (such as Atrigel by Atrix Laboratories, Inc., Fort Collins, Colo., USA) comprising a biodegradable, biocompatible polymer (s) [i.e., poly(DL-lactide), poly(DL-lactide-co-glycolide), poly(DL-lactide-co-e-caprolactone), polycaprolactone, or a combination thereof] in a biodegradable solvent (i.e., N-methyl-2-pyrrolidone). The controlled release formulation is generally injected into a patient within 5 cm, preferably 0.8 cm, from the skin surface.

The poly (DL-lactide) type polymers are solids, wherein the drug and polymers are both dissolved in a biodegradable solvent. After the injection, the biodegradable solvent diffuses out leaving behind the polymer(s) in the form of precipitated, biodegradable particles, which holds most of the androgen. As the polymer particles gradually erodes/degrades, the androgen is released into the systemic circulation. The release rate of androgen is determined by how quickly the polymer particles erodes/degrades in the body.

The active drug may also be incorporated and delivered into the storage site using different methods, such as mixing the drug with the biodegradable, biocompatible polymer(s) in a solvent, evaporating the solvent to obtain polymer particles mixed with the active drug. The size of the drug containing polymer particles should be small enough to be incorporated (not dissolved) into a suspension in a liquid (preferably an aqueous liquid). The suspension is injected into the patient's tissue proximate the skin surface. The liquid quickly leaves the depot site, leaving behind a polymer implant containing the active drug. Similarly, a care give may implant a solid piece of biocompatible bioerodable materials with the androgen incorporated therein. The implant may supply baseline testosterone needs of the patient.

The release rate from such controlled/extended release formulations is usually substantially constant during day and night. This is not the natural circadian pattern. However, controlled heat can be used to obtain a natural circadian pattern while using an ATTS having a more or less constant release rate. In the morning the user places a CHADD patch on the skin area under which the injected/implanted controlled release formulation resides. The increased temperature increases the body fluid flow surrounding the formulation and/or increases the erosion speed of the formulation matrix, resulting in increased androgen release rates and thus higher serum levels. The heating is designed to last long enough to maintain higher release rates during the day. In the afternoon or evening, the CHADD patch stops generating heat (or is removed), and release rates return to unheated levels. The user repeats this everyday. In this arrangement, a blood testosterone concentration profile that mimics the natural circadian pattern can be obtained from otherwise constant release formulations.

EXAMPLE 7

Yet another example of the present invention is similar to the invention as set forth in Example 6 except that testosterone contained in a controlled released formulation is hit onto the skin or forced into the skin by high speed impact. By way of example a caregiver can hit the controlled release formulation onto the skin at high speed using a device manufactured by Powderject Pharmaceutical, United Kingdom. Using the Powderject device, the controlled release formulation is accelerated to a speed higher than the speed of sound and then directed to collide with the patient's skin. The formulation is thereby deposited in the skin. A temperature control apparatus such as a CHADD patch is subsequently applied to the skin proximate to the entry site of the controlled release formulation on the skin. The heat generated by the CHADD patch increases the absorption and permeation of the formulation.

EXAMPLE 8

Figure 15:
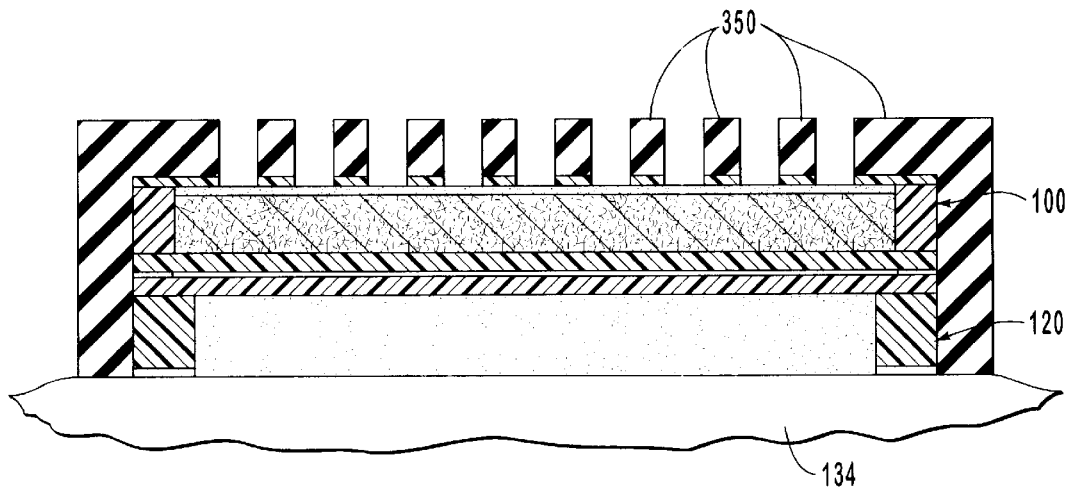

As shown in FIG. 15, an insulating material can be incorporated with the controlled temperature apparatus to assist in not only minimizing the temperature variation, but also increasing the temperature of the ATTS and the skin under it (by decreasing heat loss), each of which tend to increase dermal drug absorption.

FIG. 15 illustrates a configuration similar to that illustrated in FIG. 4 wherein the temperature control apparatus 100 of FIG. 2 is attached to the ATTS 120 of FIG. 3. The ATTS 120 is attached to a portion of the skin 134 of a patient. An insulating sleeve 350 abuts the skin 134 and encases a substantial portion of the temperature control apparatus 100 and the ATTS 120.

EXAMPLE 9

Another application of the present invention involves the use of a temperature control apparatus, such as discussed above, to mimic circadian patterns. With some drug delivery systems, mimicking circadian patterns is difficult. For example, testosterone or its derivatives, such as testosterone enanthate and testosterone cypionate, can be injected intramuscularly into men to substitute or replace diminished or absent natural testicular hormone. Testosterone enanthate and testosterone cypionate are preferred over testosterone, as they have longer duration of action than testosterone. Nevertheless, it is understood that testosterone or its derivative may be incorporated into a controlled release polymer matrix, such as poly(DL-lactide), poly(DL-lactide-co-glycolide), and poly(DL-lactide-co-(caprolactone)), to increase the duration of action. Following intramuscular injection, testosterone enanthate is absorbed gradually from the lipid tissue phase at the injection site to provide a duration of action of up to 2–4 weeks. However, natural blood testosterone concentrations in healthy man are higher in the day and lower in the night. So blood testosterone concentrations obtained from injected testosterone derivatives do not mimic the natural circadian pattern.

The present invention makes it possible to mimic circadian patterns. By way of example, a patient can inject testosterone enanthate intramuscularly, the injection should be relatively close to the skin surface. The patient then places a heating patch on the injection site every morning (until all the injected testosterone enanthate is depleted). The heating patch quickly increases the temperature of the injection site to a narrow range, and maintains it there for a desirable duration of time (i.e., about 8 hours). The heating causes increased release of testosterone enanthate and/or increased rate of conversion from testosterone enanthate to testosterone, and, thus, higher blood testosterone concentrations. The "used-up" heating patch is removed before a new heating patch is placed on the same site. Using this intermittent heat application technique, blood testosterone concentrations are low in the night and high in the day, thus mimicking the natural circadian pattern.

EXAMPLE 10

In another example of using the present invention, the user places an activated integrated ATTS/CHADD patch upon waking up in the morning (e.g., 7:00 a.m.). The CHADD patch will heat the androgen transdermal therapeutic system for 3–4 hours before the heat generated by the CHADD patch dies off gradually. Using such a system, the user gets a peak testosterone concentration around 10:00 to 11:00 a.m., thus mimicking natural circadian patterns of testosterone concentration in the blood. The user continues to wear the integrated patch and removes it before retiring to bed. Because of the shortened onset time, the user only needs to wear the ATTS for 14–16 hours rather than an extended 24 hour period. This shortened exposure to the ATTS may reduce skin irritation often associated with prolonged contact between the patient's skin and the ATTS, especially when the ATTS includes a permeation enhancer. Moreover, the user receives the advantage of an androgen transdermal therapeutic system which can mimic circadian patterns, and which does not require the user to wear the patch for 24 hours.

EXAMPLE 11

In another example of the present invention, the CHADD patch is used in conjunction with an ATTS having an androgen such as testosterone contained within a matrix formulation. The matrix formulation is in direct contact with the skin of the patient. The testosterone within the matrix formulation is released from the formulation and absorbed into the skin of the patient. Thus no rate limiting membrane is present in the ATTS to control the rate at which the testosterone is released from the matrix and absorbed into the skin. An activated CHADD patch is then placed proximate to the ATTS with the matrix formulation. The heat generated by the CHADD patch increases the diffusion coefficient of the testosterone molecules within the matrix formulation. By increasing the diffusion coefficient of the testosterone, the CHADD patch allows for increased absorption of the testosterone molecules into the patient.

EXAMPLE 12

Figure 16:
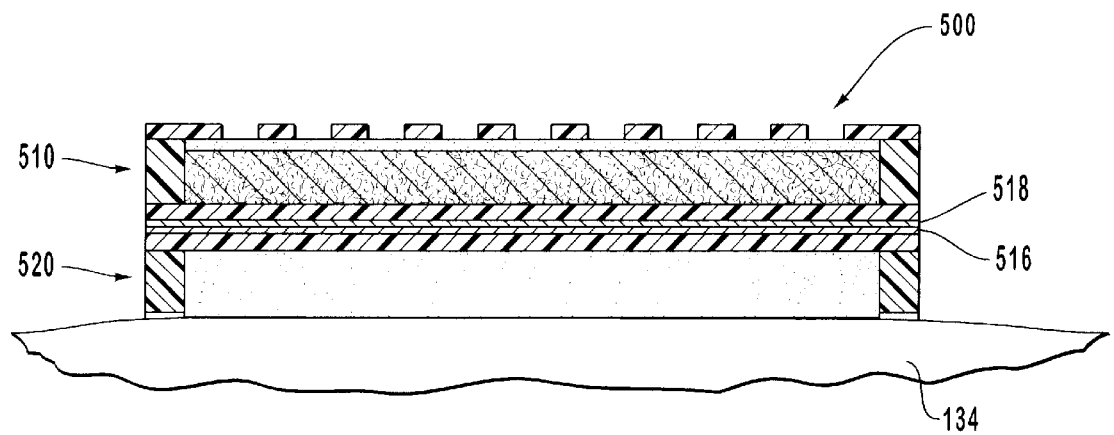
Figure 17:
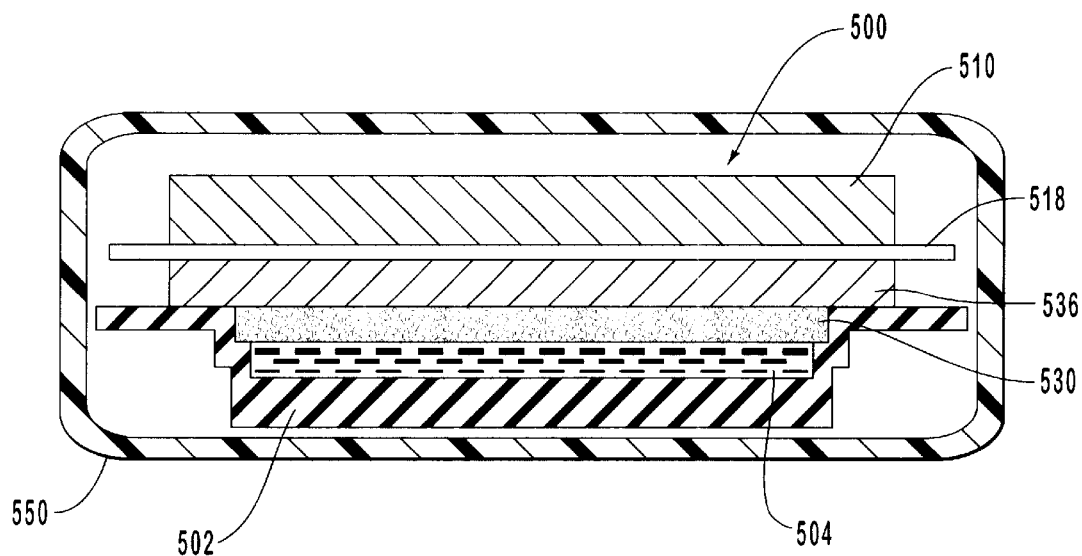

An example of using the apparatus in FIGS. 16 and 17 comprises administering an integrated patch capable of delivering the therapeutic agent and delivering controlled heat to the skin of the patient thereby mimicking natural circadian patterns. The user places the activated integrated patch on first thing in the morning (i.e. 7:00 am), which quickly reaches a steady state temperature between about 41° and about 44° C. Heating from the integrated patch lasts for 3–4 hours before the oxidation reaction which provides the heat for the heating element is complete, and no further heat is generated. Thus the testosterone concentration in the user's blood stream peaks around 10:00 or 11:00 a.m. and gradually decreases after that. The user continues to wear the patch after the heat generating element no longer generates heat, and removes the integrated patch before retiring to bed in the evening. Thus the user's serum testosterone concentration vs. time profile during the day is similar to a healthy person's natural circadian pattern. Moreover, the contact time between the skin and the integrated patch is limited to about 16 hours, rather than 24 hours, which can reduce skin irritation.

FIG. 16 is similar to FIG. 4 generally, but shows an embodiment of a temperature control apparatus integrated with an androgen transdermal therapeutic system(integrated patch 500) positioned on skin 134. The integrated patch 500 comprises a combination heating patch element 510 and androgen application element 520. Heating patch element 510 is secured to a heat sealable film 516 by an adhesive layer 518. The heating patch element 510 may be a temperature control apparatus modified to allow the temperature control apparatus to be combined with the androgen application element 520. For example, the size and shape of the temperature control apparatus may be modified to more readily combine with an androgen application element 520. Furthermore, a barrier such as heat sealable film 516 may be placed between the heating patch element 510 and the androgen application element 520 to prevent interaction between the temperature control apparatus of the heating patch element 510 and the androgen application element 520. Androgen application element 520 is secured to the heat sealable film. The androgen application element may be similar to any of the androgen transdermal therapeutic systems mentioned above. For example, the drug formulation may come into direct contact with the skin as shown in FIG. 50, or may include a rate limiting membrane (not shown). The integrated patch is packaged such that the drug formulation and the temperature control mechanism do not significantly react with each other or with external elements while in the package.

FIG. 17 shows another embodiment a temperature control apparatus integrated with an androgen transdermal therapeutic system (integrated patch 500). In this embodiment the androgen drug formulation 504 is housed in a molded polyethylene tray 502 that protects the formulation 504 both structurally and chemically (preventing solvent loss and substance transfer). The gauze layer 530 is coated with a gelling agent which, upon contact with the liquid formulation, causes the liquid formulation in the tray 502 to become a solid gel. A high-barrier medical packaging film 536 covers the formulation from the top and is heat-sealed to the tray 502 in order to further prevent the loss of moisture from the formulation 504. The gauze layer 530 which becomes embedded in the drug formulation 504, is also heat-sealed to the film 536 so that when the heat-sealed film 536 is peeled from the tray 502, it pulls the gauze 530 and attached drug formulation 504 cleanly out of the tray. The heating patch element 510 is affixed to the heat-sealed film 536 by means of an adhesive layer 518 which also provides the means of securing the system to the skin surface. The integrated androgen patch is then packaged in an air-tight foil pouch 550 which provides an excellent barrier to both oxygen and moisture.

An integrated heating patch and transdermal delivery system may provide more convenience to the user in the application of the drug therapy. In an integrated patch where the heating patch is more permanently attached to the transdermal drug delivery system, the heating patch is more securely attached and less likely to be inadvertently removed or knocked loose from the transdermal delivery system or the patient. The integrated patch may improve the likelihood of proper use of the heating patch and transdermal delivery system particularly under circumstances in which a patient feels inconvenienced when using a separate heating patch and androgen transdermal therapeutic system. Thus an integrated patch improves the chances the patient will properly use the temperature control apparatus and ATTS, thereby improving the patient's chances of receiving the desired drug dosage.

An integrated patch may be less expensive to manufacture and purchase when compared to costs of manufacturing, distributing and selling a separate temperature control apparatus and androgen transdermal therapeutic system. Such an integrated patch may also prevent a waste of resources in producing two separate devices.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed:

1. A method of increasing the delivery rate of an androgen transdermal therapeutic system through skin to correspond to a natural circadian pattern, the method comprising:
   applying an androgen transdermal therapeutic system to the skin for delivery of androgen;
   applying an apparatus capable of generating heat proximate the androgen transdermal therapeutic systems and configured to create heat in a manner that mimics the endogenous circadian androgen production; and
   heating the androgen transdermal therapeutic system with the apparatus capable of generating heat at a safe, pre-designed temperature for a safe, pre-designed length of time to achieve an increased rate of delivery of androgen through the skin to simulate to a natural circadian pattern.

2. The method of claim 1, wherein the step of applying the apparatus capable of generating heat proximate to the androgen transdermal therapeutic system comprises applying a temperature modification apparatus to the androgen transdermal therapeutic systems.

3. The method of claim 1, wherein the step of heating the androgen transdermal therapeutic system includes heating said skin to a temperature of between about 38 and 45° C.

4. The method of claim 1, wherein the step of heating the androgen transdermal therapeutic system includes heating said skin to a temperature of between about 39 and 43° C.

5. The method of claim 1, wherein the step of heating the androgen transdermal therapeutic system includes heating said skin up to a temperature of about 50° C.

6. The method of claim 1, wherein the step of heating the androgen transdermal therapeutic system effectuates an increase in the rate of androgen delivery to the human body through increasing skin permeability.

7. The method of claim 1, wherein the step of heating the androgen transdermal therapeutic system effectuates an increase in the rate of androgen delivery through increasing the permeability of blood vessel walls in the skin and subskin tissues.

8. The method of claim 1, wherein the step of heating the androgen transdermal therapeutic system effectuates an increase in the rate of androgen delivery to the human body through increasing circulation of body fluid in the skin and subskin tissues proximate the androgen transdermal therapeutic systems.

9. The method of claim 1, further including the step of reducing heating of the skin under the androgen transdermal therapeutic system with the temperature modification apparatus after a desired concentration of target androgen in the human body is achieved after a predetermined period of time.

10. The method of claim 1, further including the step of removing the temperature modification apparatus when a desired concentration of target androgen in the human body is achieved.

11. The method of claim 1, wherein the delivery system androgen is testosterone.

12. The method of claim 1, wherein the delivery system androgen is a testosterone derivative.

13. The method of claim 1, wherein the temperature modification apparatus comprises a chamber containing a medium capable of generating heat when exposed to oxygen.

14. The method of claim 1, wherein the temperature modification apparatus comprises a chamber containing reactants capable of undergoing exothermic oxidation when exposed to oxygen.

15. The method of claim 13, wherein the medium capable of generating heat when exposed to oxygen comprises iron powder and activated carbon.

16. The method of claim 13, wherein the chamber is comprised of parts being substantially impermeable to oxygen and a structure which allows a predetermined flow rate of ambient oxygen into said medium capable of generating heat inside said chamber.

17. The method of claim 16, wherein said structure comprises a cover substantially impermeable to oxygen, said cover having holes, the holes being covered by a membrane with selected oxygen permeability.

18. The method of claim 1, wherein the increased rate of delivery of the delivery system androgen through the skin is sufficient to provide a desired increased concentration of the target androgen in the systemic circulation.

19. The method of claim 1, wherein the increased rate of delivery of androgen through the skin is used to facilitate the establishment of target androgen concentration vs. time relationship that mimics the natural human circadian pattern.

20. The method of claim 19, including the step of discontinuing the heating when the desired concentration of androgen in the systemic circulation in the body is achieved.

21. The method of claim 20, the step of heating the androgen transdermal therapeutic system continues for a predetermined time, the predetermined time of heating being a time sufficient to obtain desired increased concentration levels of androgen within a patient's systemic circulation.

22. The method of claim 20, wherein the predetermined time is between one and five hours following the initiation of the heating step.

23. A method of reducing the time it takes to achieve a desired, increased concentration of a target androgen in a systemic circulation of a human body comprising:
   applying an androgen transdermal therapeutic system to the skin of the human body for delivery of therapeutic androgen to the systemic circulation of the human body;
   applying a temperature control apparatus capable of generating heat proximate the androgen transdermal therapeutic system and configured to create heat in a manner that mimics the endogenous circadian androgen production; and
   heating the skin under the androgen transdermal therapeutic systems with the temperature control apparatus to reduce the time it takes to achieve a desired increased concentration of the target androgen in the systemic circulation of the human body.

24. The method of claim 23, wherein the step of applying the temperature control apparatus capable of generating heat proximate the androgen transdermal therapeutic system further comprises applying the temperature control apparatus directly to the androgen transdermal therapeutic systems.

25. The method of claim 23, wherein the step of heating the androgen transdermal therapeutic system includes heating the skin to a temperature of between about 38 and 45° C.

26. The method of claim 23, wherein the step of heating the skin under the androgen transdermal therapeutic system includes heating the skin to a temperature of between about 39 and 43° C.

27. The method of claim 23, wherein the step of heating the skin under the androgen transdermal therapeutic system includes heating the skin up to a temperature of about 50° C.

28. The method of claim 23, wherein the step of heating the skin under the androgen transdermal therapeutic system effectuates reducing the time it takes to achieve a desired, increase concentration of the target androgen in said systemic circulation of said human body through increasing skin permeability by heating.

29. The method of claim 23, wherein the step of heating the skin under said androgen transdermal therapeutic system effectuates reducing the time it takes to achieve a desired, increase concentration of the target androgen in the systemic circulation of the human body through increasing the permeability of blood vessel walls in sub-skin tissues by the heating.

30. The method of claim 23, wherein the step of heating the skin under the androgen transdermal therapeutic system effectuates reducing the time it takes to achieve a desired, increase concentration of the target androgen in the systemic circulation of the human body through increasing circulation of body fluid proximate the transdermal androgen deliver system by heating.

31. The method of claim 23, further comprising the step of reducing said heating of the skin under the androgen transdermal therapeutic system with the temperature control apparatus after a desired increase in concentration of target androgen in the systemic circulation in the human body is achieved.

32. The method of claim 23, wherein the desired increase in concentration of the target androgen in the systemic circulation in the human body is a concentration which facilitates the mimicking of natural human circadian patterns.

33. The method of claim 23, wherein the desired increase in concentration of the target androgen is achieved between the range of about one to about five hours after the step of applying the temperature control apparatus.

34. The method of claim 33, wherein the desired increased concentration of the target androgen in the systemic circulation in the human body is a concentration which facilitates the mimicking of natural human circadian patterns.

35. The method of claim 34, wherein the concentration peaks in the morning.

36. The method of claim 35, wherein the target androgen is testosterone.

37. The method of claim 23, wherein the temperature control apparatus comprises a chamber containing a medium capable of generating heat when exposed to oxygen.

38. The method of claim 23, wherein the temperature control apparatus comprises a chamber containing reactants capable of undergoing exothermic oxidation when exposed to oxygen.

39. The method of claim 37, wherein the medium capable of generating heat when exposed to oxygen comprises an iron powder and activated carbon formulation.

40. The method of claim 37, wherein the chamber is comprised of parts being substantially impermeable to oxygen and a structure which allows a predetermined flow rate of ambient oxygen into the medium capable of generating heat inside the chamber.

41. The method of claim 40, wherein said structure comprises a cover substantially impermeable to oxygen, the cover defining holes, the holes being covered by a membrane with selected oxygen permeability.

42. The method of claim 23, wherein the increased rate of delivery of androgen through the skin is sufficient to provide a desired increased concentration of the target androgen in the systemic circulation, the desired concentration being a concentration which facilitates the mimicking of natural human circadian patterns.

43. The method of claim 42, including the step of discontinuing the heating when the desired increased concentration of the target androgen in the systemic circulation in the body is achieved.

44. The method of claim 43, wherein the step of heating the skin under the androgen transdermal therapeutic system continues for a predetermined time.

45. The method of claim 44, wherein the predetermined time of heating is a time sufficient to obtain a desired increased concentration of the target androgen within a patient's systemic circulation.

46. The method of claim 45, wherein the predetermined time is between the range of about one and five hours following the initiation of the heating step.

47. A method for adjusting a rate of androgen delivery from an androgen transdermal therapeutic system through the skin to mimic a natural circadian pattern, the method comprising:
placing an androgen transdermal therapeutic system on the skin applying a temperature control apparatus configured to create heat in a manner that mimics the endogenous circadian androgen production;
heating the skin under said androgen transdermal therapeutic system to a safe, predetermined temperature range for a safe, predesigned length of time; and
terminating said heating after the predesigned length of time to mimic the natural circadian pattern.

48. The method as claimed in claim 47, wherein the androgen is testosterone.

49. The method as claimed in claim 47 wherein the androgen is a derivative of testosterone.

50. The method of claim 47 further comprising the step of reducing said heating.

51. The method of claim 50 further comprising the steps of repeating the steps of heating the skin and reducing said heating.

52. A method for obtaining varying serum androgen release rates into the systemic circulation of the human body that correspond to a natural circadian pattern from otherwise substantially constant release delivery systems injected or implanted in said human body, the method comprising:
administering a controlled/extended release androgen therapeutic system in a target site within 3 cm from the skin surface, applying a control heating apparatus on the skin proximate to the target site configured to create heat in a manner that mimics the endogenous circadian androgen production; and
heating the androgen therapeutic system to a safe, predesigned temperature for a safe, predesigned length of time to correspond to the natural circadian pattern.

53. The method as claimed in claim 52, wherein the step of administering controlled release androgen therapeutic system comprises injecting an extended release androgen formulation.

54. The method as claimed in claim 53, wherein the step of applying a controlled heating apparatus on the skin proximate to the target site comprises placing a CHADD patch on the skin above the implanted formulation in the morning to mimic the natural circadian pattern of testosterone concentrations in the systemic circulation of a human body.

55. The method of claim 54 wherein the CHADD patch comprises a chamber defined by a bottom wall, a top wall and side walls, the bottom wall, top wall and side walls of the chamber being made of flexible substantially air impermeable material, the air impermeable material defining at least one hole through material, and a temperature regulating mechanism disposed within the chamber, the temperature regulating mechanism comprising reactants capable of creating an exothermic oxidation reaction when exposed to oxygen.

56. The apparatus as in claim 55, wherein the temperature regulating mechanism comprises a mixture of activated carbon, iron powder, and water.

57. A method of mimicking a variation of testosterone concentrations in the blood of the human body according to a natural circadian pattern, the method comprising the steps of:

administrating an integrated patch capable of delivering androgen and capable of delivering controlled heat in a manner that mimics the endogenous circadian androgen production to the skin of a patient;

elevating the patient's skin temperature proximate to the integrated patch to a safe, predesigned temperature for a safe, predesigned length of time using controlled heat, thereby allowing increased absorption of androgen that human body according to the natural circadian pattern; and maintaining said increased absorption by said controlled heat for the predesigned length of time.

58. The method of claim 55, where in the desired period of time is in the range of about 1–10 hours and the step of administering the patch is done in the morning to properly mimic the patient's natural circadian pattern.

* * * * *